(12) United States Patent
Leonardi et al.

(10) Patent No.: US 6,403,594 B1
(45) Date of Patent: Jun. 11, 2002

(54) BENZOPYRAN DERIVATIVES

(75) Inventors: Amedeo Leonardi, Milan; Gianni Motta, Barlassina; Carlo Riva, Varese; Giorgio Sironi, Pieve Emanuele, all of (IT)

(73) Assignee: Recordati, S.A. Chemical and Pharmaceutical Company, Chiasso (CH)

( * ) Notice: Subject to any disclaimer, the term of this patent is extended or adjusted under 35 U.S.C. 154(b) by 0 days.

(21) Appl. No.: 09/691,770

(22) Filed: Oct. 18, 2000

Related U.S. Application Data
(60) Provisional application No. 60/218,721, filed on Jul. 17, 2000.

(30) Foreign Application Priority Data

Oct. 18, 1999 (IT) .......................................... MI99A2174

(51) Int. Cl.$^7$ ..................... A61K 31/496; C07D 405/12
(52) U.S. Cl. ................... 514/254.11; 544/376
(58) Field of Search ...................... 544/376; 514/254.11

(56) References Cited

U.S. PATENT DOCUMENTS

| | | |
|---|---|---|
| 4,089,969 A | 5/1978 | Muchowski et al. ......... 424/274 |
| 5,091,182 A | 2/1992 | Ong et al. .................... 424/400 |
| 5,403,842 A | 4/1995 | Leonardi et al. ............. 514/252 |
| 5,474,994 A | 12/1995 | Leonardi et al. ............. 514/218 |
| 5,605,896 A | 2/1997 | Leonardi et al. ............. 514/218 |
| 6,071,920 A | 6/2000 | Leonardi et al. ............. 514/255 |

FOREIGN PATENT DOCUMENTS

| | | | |
|---|---|---|---|
| EP | 0 558 245 A | 9/1993 | ......... C07D/311/30 |
| EP | 0 625522 A1 | 11/1994 | ........... C07F/9/655 |
| EP | 0 625522 B1 | 11/1994 | ........... C07F/9/655 |
| EP | 0 748800 A2 | 12/1996 | ......... C07D/239/54 |
| WO | WO 99/06382 A | 2/1999 | ......... C07D/295/10 |
| WO | WO 99/06384 A | 2/1999 | ......... C07D/295/12 |

OTHER PUBLICATIONS

Albertson, Noel F, "Synthesis of Peptides With Mixed Anhydrides"; in *Organic Reactions;* vol. 12, chapter 4, pp. 157–363 (1962).
Andersson, K.E, et al., "Benign Prostatic Hyperplasia and α–Adrenoceptors in the Lower Urinary Tract"; *4$^{th}$ Intl. Consult. in BPH Paris*, Jul. 2–5, 601–609 (1997).
Andersson, K. E, "Mode of Action of $\alpha_1$–Adrenoreceptor Antagonists in the Treatment of Lower Urinary Tract Symptoms", *BJU International*, 85:12–18 (2000).
Basha, Anwer, et al., "A Mild, General Method for Conversion of Esters to Amides", *Tetrahedron Letters*, 48:4171–4174 (1977).
Brougham, Paul, et al., "Oxidation Reactions Using Magnesium Monoperphthalate: A Comparison with m–Chloroperoxybenzoic Acid" *Synthesis*, 1015–1017 (1987).

Bryan, J.D, "Synthesis of the 7–Chloro–derivatives of Chromone, Flavone, and Isoflavone": *J. Chem. Soc. Perkin Trans.* 1:1279–1281 (1960).
Cheng, Yung–Chi, et al., "Relationship Between the Inhibition Constant ($K_1$) and the Concentration of Inhibitor Which Causes 50 Per Cent Inhibition ($I_{50}$) of an Enzymatic Reaction", *Biochemical Pharmacology*, 22:3099–3108 (1973).
Cotecchia, Susanna, et al., "Molecular Cloning and Expression of the cDNA for the Hamster $\alpha_1$–Adrenergic Receptor", *Proc. Natl. Acad. Sci. USA*, 85:7159–7163 (1988).
Cullen, Bryan R, "Use of Eukaryotic Expression Technology in the Functional Analysis of Cloned Genes", *Methods in Enzymology*, 152:684–704 (1987).
DeLean, A, et al.; "Simultaneous Analysis of Families of Sigmoidal Curves: Application to Bioassay, Radioligand Assay, and Physiological Dose–Response Curves"; *Am. J. Physiol*, 235:E97–E102 (1978).
Doherty, Annette, M, et al., "Design and Synthesis of Potent, Selective, and Orally Active Fluorine–Containing Renin Inhibitors"; *J. Med. Chem.*, 35:2–14 (1992).
Elworthy, T.R, et al., "N–Arylpiperazinyl–N'–Propylamino Derivatives of Heteroaryl Amides as Functional Uroselective $\alpha_1$–Adrenoceptor Antagonists", *J. Med. Chem.* 40:2674–2687 (1997).
Fargin, Annick, et al., "Effector Coupling Mechanisms of the Cloned 5–HT1A Receptor"; *J. Biological Chemistry;* 284:14848–14852 (1989).

(List continued on next page.)

*Primary Examiner*—Emily Bernhardt
(74) *Attorney, Agent, or Firm*—Darby & Darby

(57) ABSTRACT

The invention relates to novel benzopyran derivatives of formula I, their N-oxides and pharmaceutically acceptable salts thereof. The compounds are endowed with enhanced selectivity for alpha1-adrenergic receptors and a low activity in lowering blood pressure. The compounds are useful in the treatment of obstructive syndromes of the lower urinary tract, including benign prostatic hyperplasia (BPH), and in the treatment of lower urinary tract symptoms (LUTS), neurogenic lower urinary tract dysfunction (NLUTD), and other conditions.

(I)

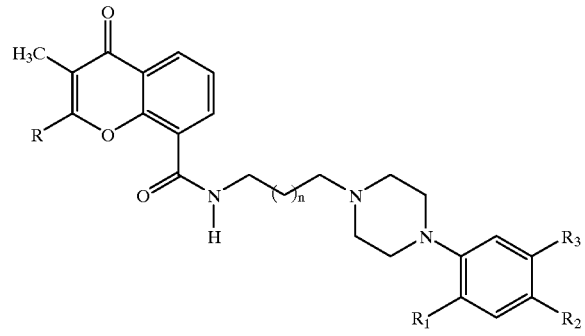

38 Claims, No Drawings

OTHER PUBLICATIONS

Fargin, Annick, et al., "The Genomic Clone G–21 Which Resembles a β–Adrenergic Receptor Sequence Encodes the 5–HT $_{1A}$ Receptor"; *Nature;* 335:358–360 (1988).

Fitzpatrick, J, "Facts and Future Lines of Research in Lower Urinary Tract Symptoms in Men and Women: An Overview of the Role of $\alpha_1$–Adrenoreceptor Antagonists", *BJU International.,* 85(Suppl.2):1–5 (2000).

Flavahan, N.A, et al., "$\alpha_1$_Adrenoreceptor Subclassification in Vascular Smooth Muscle", *Trends Pharmacol. Sci,,* 7:347–349 (1986).

Ford, Anthony, P.D.W, et al., "Do$\alpha_{1A}$ ($\alpha_{1C}$)–Adrenoreceptors (AR) Mediate Prostatic Smooth Muscle Contraction in Man? Studies with a Novel, Selective $\alpha_{1A}$–AR Antagonist, RS 17053", *Br. J. Pharmacol,* 114:24 P (1995).

Furchgott, Robert F, "The Classification of Adrenoceptors (Adrenergic Receptors). An Evaluation From the Standpoint of Receptor Theory", in *Handbook of Experim. Pharmacology—New Series,* Chap. 9, pp. 283–335 (1972).

Gibson, M.S, "The Introduction of the Amino Group", in *The Chemistry of the Amino Group,* S Patai (Ed.), John Wiley & Sons, N.Y., Chapter 2, pp. 37–66 (1968).

Gozlan, H, et al., "Photoaffinity Labelling and Solubilization of the Central 5–HT$_{1A}$ Receptor Binding Site", *J. Receptor Res.,* 7:195–221 (1987).

Haines, Alan H, *Methods for the Oxidation of Organic Compounds,* Academic Press, Chapter 3, pp. 146–152 (1985).

Hendrickson, James. B, et al., "Triflamides: New Acylating and Triflating Reagents", *Tetrahedron Letters,* 46:4607–4610 (1973).

Hieble, Paul, J, et al., "International Union of Pharmacology X. Recommendation for Nomenclature of $\alpha_1$–Adrenoreceptors: Consensus Update", *Pharmacol. Rev.,* 47:267–270 (1995).

Imagawa, Jun–Ichi, et al., "Functional Evaluation of Sympathetically Mediated Responses in In Vivo Lower Urinary Tract of Dogs", *J. Pharmacol,* Methods, 22:103–111 (1989).

Ishihara, Yuji, et al., "Central Cholinergic Agents. II. $^{1)}$ Synthesis and Acetylcholinesterase Inhibitory Activities of N–[ω[N–Alkyl–N–(phenylmethyl) amino]alkyl]–3–arylpropenamides", *Chem. Pharm. Bull,* 39: 3236–3243 (1991).

Kakizaki, H, et al., "Current View and Status of the Treatment of Lower Urinary Tract Symptoms and Neurogenic Lower Urinary Tract Dysfunction", BJU Intl. 85(Suppl.2):25–30 (2000).

Kenny, B.A, et al., "Evaluation of the Pharmacological Selectivity Profile of $\alpha_1$ Adrenoceptor Antagonists at Prostatic $\alpha_1$ Adrenoceptors: Binding, Functional and In Vivo Studies", *Br. J. Pharmacol,* 118: 871–878 (1996).

Kobilka, Brian K, et al., "An Intronless Gene Encoding a Potential Member of the Family of Receptors Coupled To Guanine Nucleotide Regulatory Proteins", *Nature,* 329:75–79 (1987).

Leonardi, A, et al., "Pharmacological Characterization of the Uroselective Alpha–1 Antagonist Rec 15/2739 (SB 216469): Role of the Alpha–1L Adrenoceptor in Tissue Selectivity, Part 1", *J. Pharmacol. Exp. Ther.* 281:1272–1283 (1997).

Lipton, Michael, F, et al., "Conversion of Esters to Amides With Dimethylaluminum Amides: N,N–Dimethylcyclohexanecarboxamide", *Organic Syntheses.,* 59:49–53 (1979).

Malloy, Brian J, et al., "$\alpha_1$–Adrenoceptor Receptor Subtypes in Human Detrusor", *J. Urology,* 160:937–943 (1998).

March, J, *Advanced Organic Chemistry:Reactions, Mechanisms, and Structure,* 4th edit. J. Wiley & Sons, NY, pp. 491–493; 760; 1041–1042 and 1091–1092 (1992).

McGrath, J.C, et al., "Alpha–Adrenoceptors: A Critical Review", *Medicinal Research Reviews,* 9:407–533 (1989).

McGuire, Edward J, et al., "Effect of Alpha–Adrenergic Blockade and Anticholinergic Agents on the Decentralized Primate Bladder", *Neurourology and Urodynamics,* 4:139–142 (1985).

Michel, Martin, C, et al., "Radioligand Binding Studies of $\alpha_1$–Adrenoceptor Subtypes in Rat Heart", *Brit. J. Pharmacol,* 111:533–538 (1994).

Mitchell, James A, et al., "The Preparation of Aliphatic Amides", *J. Am. Chem. Soc.,* 53:1879–1883(1931).

Muramatsu, Ikunobu, et al., "Functional Subclassification of Vascular $\alpha_1$–Adrenoceptors", *Pharmacology Communications,* 6:23–28 (1995).

Prelog, V, et al., *Collect. Czech. Chem. Comm.,* 5:497–502 (1933).

Rubottom, George M, "Preparation of Methyl Ketones by the Sequential Treatment of Carboxylic Acids with Methyllithium and Chlorotrimethylsilane", *J. Org. Chem.,* 48:1550–1552 (1983).

Schwinn, Debra, A, et al., "Molecular Cloning and Expression of the cDNA of a Novel $\alpha_1$–Adrenergic Receptor Subtype", *J. Biol. Chem.,* 265:8183–8189 (1990).

Schumutz, J, "Chromon–Derivate: UV.–Absorptionsspektren; coronardilatatorische Wirkung", *Helvetica Chimica Acta,* vol. XXXIV, pp. 767–779 (1951).

Serels, Scott, et al., "Prospective Study Comparing Hyoscyamine, Doxazosin, and Combination Therapy for the Treatment of Urgency and Frequency in Women", *Neurourology and Urodynamics,* 17:31–36 (1988).

Sundin Torsten, et al., "The Sympathetic Innervation and Adrenoreceptor Function of the Human Lower Urinary Tract in the Normal State and After Parasympathetic Denervation", *Investigative Urology,* 14:322–328 (1977).

Swierzewski, Stanley J, et al., "The Effect of Terazosin on Bladder Function in the Spinal Cord Injured Patient" *J. Urology,* 151:951–954 (1994).

Takahashi, Torizo, et al., "Syntheses of Basic Phenol Alkyl Ethers. II. Derivatives of 3–Salicylaldehyde and Alkyl Phenyl Ketones", *Chemical Abstracts,* 49:1623 (1955).

Takahashi, Torizo, et al., "Syntheses of Basic Phenol", *J. Pharmacol. Soc. Jpn.,* 74:48–51 (1954).

Testa, R, et al., "Pharmacological Characterization of the Uroselective Alpha–1 Antagonist Rec 15/2739 (SB 216469): Role of the Alpha–1L Adrenoceptor in Tissue Selectivity, Part II", *J. Pharmacology and Experimental Therapeutics,* 281:1284–1293 (1997).

Testa, R, et al., "Rec 15/2739 (SB 216469): A Novel Prostate Selective $\alpha_1$–Adrenoceptor Antagonist", *Pharmacology Communications,* 6:79–86 (1995).

BENZOPYRAN DERIVATIVES

This patent application is based on Provisional Patent Application Serial No. 60/218,721, filed on Jul. 17, 2000, which is hereby incorporated by reference. Applicants claim the benefit of the filing date of the aforesaid Provisional Application under 35 U.S.C. §119(e)(1).

Applicants also claim priority under 35 U.S.C. §119(a–d) of Italian patent application no. MI99A 002174, filed Oct. 18, 1999, which is hereby incorporated by reference

SCOPE OF THE INVENTION

This invention relates to benzopyran derivatives, to pharmaceutical compositions containing them and to uses for such derivatives and compositions.

BACKGROUND OF THE INVENTION

Flavoxate, 3-methyl-4-oxo-2-phenyl-8-(2,N-piperidinylethoxycarbonyl)-4H-1-benzopyran, has the formula:

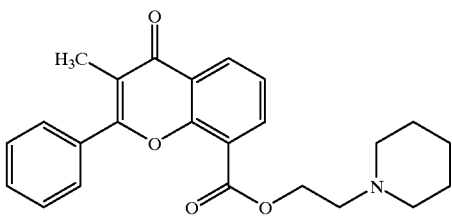

and is used as a pharmaceutical agent for urinary-tract disturbances as it possesses a smooth-muscle relaxing activity attributable to its calcium antagonist activity. This activity is exerted on the bladder-neck smooth muscles or can be related to an effect on the micturition centre in the central nervous system (Guarneri L. el al., *Drugs of Today*, 30:91–98, 1994).

U.S. Pat. No. 5,403,842, Leonardi et al., and its continuations in part (U.S. Pat. No. 5,474,994, Leonardi et al., and U.S. Pat. No. 5,605,896, Leonardi et al.) claim more complex amino functions in place of the piperidinyl group of flavoxate. Further claimed changes include alternatives to the ethoxycarbonyl group which links the amino moiety to position 8 of the benzopyran ring, alternative substitutions at positions 2, 3, 6 and 7 of the benzopyran ring, replacement of the ring heteroatom by a sulphur atom or by a sulphinyl or sulphonyl group, or by a nitrogen atom or an amino group, and/or hydrogenation at position 2–3 of the benzopyran ring. Further variations of the heterocyclic ring were also described. These structural variations gave the new compounds the ability to interact with different biological systems, as supported by the affinity of the new compounds for the $\alpha_1$-adrenergic and $5HT_{1A}$-serotoninergic receptors. Flavoxate is practically devoid of affinity for these receptors. One of the most interesting of the compounds of U.S. Pat. No. 5,403,842, Leonardi et al., was Compound A (Ex. 11).

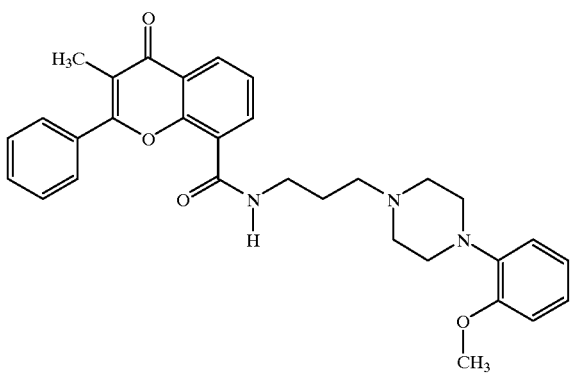

The compounds of the present invention retain the 3-methyl-4-oxo-8-[(ω-(4-phenyl-1-piperazinyl)alkylcarbamoyl]-4H-1-benzopyran structure of Compound A, but introduce alternative substituents in place of the phenyl group at position 2 of the benzopyran ring and new patterns of substitution for the phenyl group linked to the piperazine ring. These new compounds are endowed with selective antagonistic activity for the $\alpha_1$ receptor (in particular if compared to affinity for the $5-HT_{1A}$ receptor) and are able to reduce the contractility of prostatic urethra in mammals with little or no effect on blood pressure. This activity profile suggests the safer use of the compounds of the invention in the therapy of obstructive syndromes of the lower urinary tract, including benign prostatic hyperplasia (BPH), female lower urinary tract symptoms (LUTS), and neurogenic lower urinary tract dysfunction (NLUTD), without side effects associated with hypotensive activity. Some of the new compounds also have a longer duration of action on the urethra than Compound A.

SUMMARY OF THE INVENTION

The invention describes compounds of the general formula I:

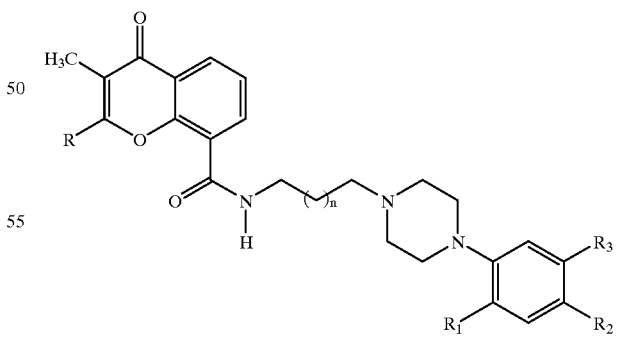

wherein

R is selected from the group consisting of a phenyl, alkoxycarbonyl, alkylcarbonyl, carbamoyl, alkylcarbamoyl, dialkylcarbamoyl, cyano and alkoxycarbonylamino group;

$R_1$ is selected from the group consisting of an alkyl, alkoxy, polyfluoroalkoxy, hydroxy and trifluoromethanesulphonyloxy group;

each of $R_2$ and $R_3$ independently is selected from a group consisting of a hydrogen, halogen, polyfluoroalkyl, polyfluoroalkoxy, cyano and carbamoyl group; and n is 0, 1 or 2;

with the proviso that, if R represents a phenyl group and both $R_2$ and $R_3$ represent hydrogen and/or halogen atoms, then $R_1$ represents a polyfluoroalkoxy or trifluoromethanesulphonyloxy group.

The invention also includes the N-oxides and pharmaceutically acceptable salts of these compounds.

When R does not represent a phenyl group, each of $R_2$ and $R_3$ preferably independently represents a hydrogen or halogen atom or a polyfluoroalkoxy group.

Alkyl and alkoxy groups preferably have from 1 to 4 carbon atoms; complex groups such as alkoxycarbonyl, alkylcarbonyl, alkylcarbamoyl, dialkylcarbamoyl, polyfluoroalkyl, polyfluoroalkoxy and alkoxycarbonylamino, are preferably construed accordingly. Preferred polyfluoroalkoxy groups are trifluoromethoxy and 2,2,2-trifluoroethoxy. The preferred value for n is 1.

Further preferred is where R is selected from the group consisting of phenyl, alkoxycarbonyl, alkylcarbonyl, carbamoyl, alkylcarbamoyl, dialkylcarbamoyl, cyano and alkoxycarbonylamino; $R_1$ is selected from the group consisting of alkoxy and hydroxy; each of $R_2$ and $R_3$ is independently selected from the group consisting of hydrogen, halogen, polyfluoroalkyl and carbamoyl; and n=0, 1 or 2.

Further preferred is where R is selected from the group consisting of carbamoyl, alkylcarbamoyl and dialkylcarbamoyl; $R_1$ is selected from the group consisting of alkoxy, polyfluroalkoxy, hydroxy and trifluoromethanesulphonyloxy; each $R_2$ and $R_3$ is independently selected from the group consisting of hydrogen, halogen, polyfluoroalkyl, polyfluoroalkoxy, cyano and carbamoyl; and n=0, 1 or 2.

Further preferred is where R is carbomoyl; $R_1$ is selected from the group consisting of alkoxy; polyfluoroalkoxy, hydroxy, and trifluoromethanesulphonyloxy; each $R_2$ and $R_3$ is independently selected from the group consisting of hydrogen, halogen, polyfluoroalkyl, polyfluoroalkoxy, cyano and carbamoyl; and n=0, 1 or 2.

The compounds of the invention include those compounds where, independently, R is selected from the group consisting of an alkoxycarbonyl, alkylcarbonyl, carbamoyl, alkylcarbamoyl, dialkylcarbamoyl, cyano and alkoxycarbonylamino group, $R_1$ is selected from a group consisting of methyl, methoxy, trifluoromethoxy, 2,2,2-trifluoroethoxy, hydroxy and trifluoromethanesulphonyloxy group, $R_2$ is selected from the group consisting of hydrogen and fluorine, $R_3$ is selected from the group consisting of hydrogen, fluorine, chlorine, trifluoromethyl, 2,2,2-trifluoroethoxy, cyano and carbamoyl; and n is 0, 1 or 2.

Other compounds within the invention are those compounds with combinations of substituents where, together, R is selected from the group consisting of an alkoxycarbonyl, alkylcarbonyl, carbamoyl, alkylcarbamoyl, dialkylcarbamoyl, cyano and alkoxycarbonylamino group and $R_1$ is selected from the group consisting of methyl, methoxy, trifluoromethoxy, 2,2,2-trifluoroethoxy, hydroxy and trifluoromethanesulphonyloxy group; or R is selected from the group consisting of an alkoxycarbonyl, alkylcarbonyl, carbamoyl, alkylcarbamoyl, dialkylcarbamoyl, cyano and alkoxycarbonylamino group and $R_2$ is selected from the group consisting of hydrogen and fluorine; or R is selected from the group consisting of an alkoxycarbonyl, alkylcarbonyl, carbamoyl, alkylcarbamoyl, dialkylcarbamoyl, cyano and alkoxycarbonylamino group and $R_3$ is selected from the group consisting of hydrogen, fluorine, chlorine, trifluoromethyl, 2,2,2-trifluoroethoxy, cyano and carbamoyl; and n is 0, 1 or 2.

Compounds of the invention also include those compounds with combinations of substituents where, together, $R_1$ is selected from the group consisting of methyl, methoxy, trifluoromethoxy, 2,2,2-trifluoroethoxy, hydroxy and trifluoromethanesulphonyloxy group and $R_2$ is selected from the group consisting of hydrogen and fluorine; or $R_1$ is selected from the group consisting of methyl, methoxy, trifluoromethoxy, 2,2,2-trifluoroethoxy, hydroxy and trifluoromethanesulphonyloxy group and $R_3$ is selected from the group consisting of hydrogen, fluorine, chlorine, trifluoromethyl, 2,2,2-trifluoroethoxy, cyano and carbamoyl; and n is 0, 1 or 2.

Also included within the invention compounds with combinations of substituents where, together, $R_2$ is selected from the group consisting of hydrogen and fluorine and $R_3$ is selected from the group consisting of hydrogen, fluorine, chlorine, trifluoromethyl, 2,2,2-trifluoroethoxy, cyano and carbamoyl; and n is 0, 1 or 2.

The invention also includes compounds having combinations of substituents where, together, R is selected from the group consisting of an alkoxycarbonyl, alkylcarbonyl, carbamoyl, alkylcarbamoyl, dialkylcarbamoyl, cyano and alkoxycarbonylamino group, $R_1$ is selected from the group consisting of methyl, methoxy, trifluoromethoxy, 2,2,2-trifluoroethoxy, hydroxy and trifluoromethanesulphonyloxy group and $R_2$ is selected from the group consisting of hydrogen and fluorine; or R is selected from the group consisting of an alkoxycarbonyl, alkylcarbonyl, carbamoyl, alkylcarbamoyl, dialkylcarbamoyl, cyano and alkoxycarbonylamino group, $R_1$ is selected from the group consisting of methyl, methoxy, trifluoromethoxy, 2,2,2-trifluoroethoxy, hydroxy and trifluoromethanesulphonyloxy group and $R_3$ is selected from the group consisting of hydrogen, fluorine, chlorine, trifluoromethyl, 2,2,2-trifluoroethoxy, cyano and carbamoyl; or R is selected from the group consisting of an alkoxycarbonyl, alkylcarbonyl, carbamoyl, alkylcarbamoyl, dialkylcarbamoyl, cyano and alkoxycarbonylamino group, $R_2$ is selected from the group consisting of hydrogen and fluorine and $R_3$ is selected from the group consisting of hydrogen, fluorine, chlorine, trifluoromethyl, 2,2,2-trifluoroethoxy, cyano and carbamoyl group; and n is 0, 1 or 2.

The compounds of the invention also include those having combinations of substituents where, together, $R_1$ is selected from the group consisting of methyl, methoxy, trifluoromethoxy, 2,2,2-trifluoroethoxy, hydroxy and trifluoromethanesulphonyloxy group, $R_2$ is selected from the group consisting of hydrogen and fluorine and $R_3$ is selected from the group consisting of hydrogen, fluorine, chlorine, trifluoromethyl, 2,2,2-trifluoroethoxy, cyano and carbamoyl; and n is 0, 1 or 2.

The compounds of the invention also include those having combinations of substituents where, together, R is selected from the group consisting of an alkoxycarbonyl, alkylcarbonyl, carbamoyl, alkylcarbamoyl, dialkylcarbamoyl, cyano and alkoxycarbonylamino group, $R_1$ is selected from the group consisting of methyl, methoxy, trifluoromethoxy, 2,2,2-trifluoroethoxy, hydroxy and trifluoromethanesulphonyloxy group, $R_2$ is selected from the group consisting of hydrogen and fluorine and $R_3$ is selected from the group consisting of hydrogen, fluorine, chlorine, trifluoromethyl, 2,2,2-trifluoroethoxy, cyano and carbamoyl.

The invention further provides pharmaceutical compositions comprising a compound of the general formula I or a N-oxide or pharmaceutically acceptable salt of such a compound in admixture with a pharmaceutically acceptable diluent or carrier. Preferences are as outlined above for the compounds of the invention.

In another aspect, the present invention is directed to methods for preventing contractions (including noradrenaline-mediated contractions) of the urethra and lower urinary tract, without substantially affecting blood pressure, by administering one or more selected compounds of the general Formula I to a mammal (including a human) in need of such treatment in an amount or amounts effective for the particular use.

In yet another aspect, the invention is directed to methods for blocking $\alpha_1$ receptors by exposing said receptors (e.g. by delivery to the environment of said receptors, by addition to an extracellular medium, or by administering to a mammal possessing said receptors) an effective amount of a compound of the invention, in this way relieving diseases associated to overactivity of said receptors.

The very high uroselectivity of the compounds of this invention has been tested in the dog model described in Example 28, where their efficacy in antagonizing the contractions of prostatic urethra in the presence of very limited effects on blood pressure has been shown, in comparison to Compound A and to other well know $\alpha_1$ antagonists, prazosin and terazosin. Accordingly, it is a primary object of the present inventi to provide a method of treating BPH which avoids any undue side effect due to acute hypotension (i.e., limited effects on blood pressure).

As used herein, "limited effect on blood pressure" and "without substantial effect on blood pressure" are defined as effects on blood pressure that are without clinical significance. In experimental animals, "limited" and "without substantial" effects on blood pressure are defined as lowering blood pressure by about 10% or less, compared to control animals. In humans, "limited" and "without substantial" effects on blood pressure are defined as effects wherein diastolic blood pressure is reduced by less than about 5 mm Hg.

It is another object of the present invention to provide pharmaceutical compositions comprising 2-substituted benzopyran-8-carboxamide derivatives which are very potent $\alpha_1$-adrenoceptor antagonists, which compositions are effective for the treatment of BPH, optionally including a carrier or diluent.

It is another object of the present invention to provide a method of treating BPH using 2-substituted benzopyran-8-carboxamide derivatives which are active as $\alpha_1$-adrenoceptor selective antagonists.

Another aspect of the invention is the use of new compounds for lowering intraocular pressure, inhibiting cholesterol biosynthesis, treatment of cardiac arrhythmia and erectile dysfunction, and reducing sympathetically-mediated pain.

It is understood that "sympathetically-mediated" is defined as any physiological sensation, condition or response that depends upon any component of the sympathetic nervous system, can be modulated by the action of any component of the sympathetic nervous system, or can be affected by treatment of any component of the sympathetic nervous system.

A further object of the present invention is the release of compounds of the present invention or pharmaceutical compositions containing compounds of the present invention in the environment of $\alpha_1$ adrenergic receptors wherein said release is effected by administering compounds of the present invention or pharmaceutical compositions containing compounds of the present invention to a mammal including a human possessing said receptors.

A further object of the present invention is the method of treatment of a patient suffering from benign prostatic hyperplasia, the method comprising administering an effective amount of a compound of the present invention or a pharmaceutical composition containing a compound of the present invention to a patient in need of such treatment.

A further object of the present invention is the method of treatment of a patient suffering from excessive intraocular pressure, the method comprising administering an effective amount of a compound of the present invention or a pharmaceutical composition containing a compound of the present invention to a patient in need of such treatment.

A further object of the present invention is the method of treatment of a patient suffering from cardiac arrhythmia, the method comprising administering an effective amount of a compound of the present invention or a pharmaceutical composition containing a compound of the present invention to a patient in need of such treatment.

A further object of the present invention is the method of treatment of a patient suffering from erectile dysfunction, the method comprising administering an effective amount of a compound of the present invention or a pharmaceutical composition containing a compound of the present invention to a patient in need of such treatment.

A further object of the present invention is the method of treatment of a patient suffering from sexual dysfunction, the method comprising administering an effective amount of a compound of the present invention or a pharmaceutical composition containing a compound of the present invention to a patient in need of such treatment.

A further object of the present invention is the method for inhibiting cholesterol biosynthesis, the method comprising administering an effective amount of a compound of the present invention or a pharmaceutical composition containing a compound of the present invention to a patient in need of such treatment.

A further object of the present invention is the method for reducing sympathetically mediated pain, the method comprising administering an effective amount of a compound of the present invention or a pharmaceutical composition containing a compound of the present invention to a patient in need of such treatment.

A further object of the present invention is the method for the treatment of lower urinary tract symptoms (LUTS), which include but are not limited to filling symptoms, urgency, incontinence and nocturia, as well as voiding problems such as weak stream, hesitance, intermittency, incomplete bladder emptying and abdominal straining, the method comprising administering an effective amount of a compound of the present invention or a pharmaceutical composition containing a compound of the present invention to a patient in need of such treatment, optionally further comprising the inclusion of an anticholinergic compound which may be selected from the group consisting of tolterodine, oxybutinin, darifenacin, alvameline and temiverine.

A further object of the present invention is the method for the treatment of neurogenic lower urinary tract dysfunction (NLUTD), the method comprising administering an effective amount of a compound of the present invention or a pharmaceutical composition containing a compound of the present invention to the patient, optionally further comprising the inclusion of an anticholinergic compound which may be selected from the group consisting of tolterodine, oxybutinin, darifenacin, alvameline and temiverine.

A further object of the present invention is the treatment of LUTS in females which include but are not limited to filling symptoms, urgency, incontinence, and nocturia as well as voiding problems such as weak stream, hesitance, intermittency, incomplete bladder emptying, and abdominal straining, the method comprising administering an effective amount of a compound of the present invention or a pharmaceutical composition containing a compound of the present invention to a woman in need of such treatment, optionally further comprising the inclusion of an anticholinergic compound which may be selected from the group consisting of tolterodine, oxybutinin, darifenacin, alvameline and temiverine Other features and advantages of the present invention will be apparent to those skilled in the art from the following detailed description and claims.

DETAILED DESCRIPTION OF THE INVENTION

All patents, patent applications, and literature references cited in this application are incorporated by reference in their entirety.

It is understood that all compounds described, listed and represented herein are meant to include all enantiomers or mixtures of enantiomers, hydrates, solvates, polymorphs and pharmaceutically acceptable salts thereof.

The adrenergic antagonistic activity of the compounds of the invention renders them useful as agents acting on body tissues particularly rich in $\alpha_1$ adrenergic receptors (such as prostate, urethra and bladder). Accordingly, the antiadrenergic compounds within the invention, established as such on the basis of their receptor binding profile, can be useful therapeutic agents for the treatment, for example, of micturition problems associated with obstructive disorders of the lower urinary tract, including but not limited to benign prostatic hyperplasia (BPH).

BPH is a progressive condition, which is characterized by a nodular enlargement of prostatic tissue resulting in obstruction of the urethra. This results in increased frequency of urination, nocturia, a poor urinary stream and hesitancy or delay in starting urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the ageing male population. BPH is observed in approximately 70% of males over the age of 70. Currently, the specific method of choice for treating BPH is surgery. A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

$\alpha$-Adrenergic receptors (McGrath, J. C. et al., *Med. Res. Rev.* 9:407–533, 1989) are specific neuroreceptor proteins located in the peripheral and central nervous systems on tissues and organs throughout the body. These receptors are important targets for controlling many physiological functions and, thus, represent important objectives for drug development. In fact, many $\alpha$ adrenergic drugs have been developed over the past 40 years. Examples include clonidine, phenoxybenzamine and prazosin, terazosin, alfuzosin, doxazosin, tamsulosin (treatment of hypertension), naphazoline (nasal decongestant), and apraclonidine (treating glaucoma). $\alpha$-Adrenergic drugs can be broken down into two distinct classes: agonists (clonidine and naphazoline are agonists), which mimic the receptor activation properties of the endogenous neurotransmitter noradrenaline, and antagonists (phenoxybenzamine and prazosin, terazosin, alfuzosin, doxazosin and tamsulosin are antagonists), which act to block the effects of noradrenaline. Many of these drugs are effective, but also produce unwanted side effects (for example, clonidine produces dry mouth and sedation in addition to its antihypertensive effect).

The above reported agonists are selective for the $\alpha_2$ adrenergic receptor whereas most antagonists are selective for the $\alpha_1$ adrenoceptor, with the exception of tamsulosin which shows a comparable affinity also for the $5\text{-HT}_{1A}$ receptor. Many of the cited $\alpha_1$ antagonists are currently used for the therapy of BPH but, due to their poor uroselectivity, they are liable to cause cardiovascular side effects.

Recent pharmacological, biochemical and radioligand-binding studies evidenced three different $\alpha_1$-receptor subtypes with a high affinity for prazosin, namely $\alpha_{1A}$-($\alpha_{1a}$-), $\alpha_{1B}$-($\alpha_{1b}$-) and $\alpha_{1D}$-($\alpha_{1d}$-), with lower case subscripts being used for recombinant receptors and upper case subscripts for receptors in native tissues (Hieble P. et al., *Pharmacol. Rev.*, 47: 267–270, 1995). In functional studies $\alpha_1$ receptors with a low affinity for prazosin have also been identified and termed $\alpha_{1L}$ receptors (Flavahan et al., *Trends Pharmacol. Sci.*, 7: 347–349, 1986; Muramatsu et al., *Pharmacol. Comm.*, 6: 23–28, 1995).

Several studies have demonstrated the presence of these $\alpha_1$-adrenergic receptor subtypes in the lower-urinary-tract tissues (Andersson K. E., "$4^{th}$ *International Consultation in Benign Prostatic Hyperplasia* (BPH)", Paris, Jul. 2–5, 1997, pages 601–609).

Several studies have shown that the human prostate receives innervation from both the sympathetic and parasympathetic nervous systems.

The adrenergic nerves are considered responsible for prostatic smooth muscle tone by releasing noradrenaline, stimulating contraction-mediating $\alpha_1$-adrenoceptors. Approximately 50% of the total urethral pressure in BPH patients may be due to $\alpha_1$-adrenoceptor-mediated muscle tone. Functional studies have indicated the occurrence of important adrenoceptor functions in prostatic adenomatous and capsular tissue. Clinical studies with the prototypical $\alpha_1$-adrenoceptor selective antagonist, prazosin, enforced the key role of $\alpha_1$ adrenoceptors in the control of prostatic smooth-muscle tone. This was also confirmed in the laboratory by studies showing that, although both $\alpha_1$ and $\alpha_2$ adrenoceptors can be identified within the human prostate, the contractile properties are mediated primarily by $\alpha_1$ adrenoceptors. Many clinical investigations have confirmed that $\alpha_1$-adrenoceptor blockade relieves lower-urinary-tract symptoms (LUTS), both of irritative and obstructive type, in patients with BPH.

Lower urinary tract symptoms (LUTS) also develop in women as they age. As in men, LUTS in women includes both filling symptoms such as urgency, incontinence, and nocturia, and voiding symptoms, such as weak stream, hesitancy, intermitency, incomplete bladder emptying and abdominal straining. That both men and women experience a similar high prevalence of filling and voiding LUTS suggests that at least part of the underlying etiology may be identical. In a recent study, an $\alpha_1$-antagonist was reported to reduce LUTS in women to a greater extent than an anticholinergic (Serels, S. and Stein, M., *Neurology and Urodynamics* 17: 31–36, 1998). The authors concluded that there appeared to be a role for $\alpha_1$-antagonists in treating LUTS in women. The possible mechanisms implicated to explain these results are: a) dysfunction of the bladder neck and urethra, causing functional outlet obstruction, analogous to BPH-induced outlet obstruction, with secondary detrusor overactivity; and b) increased $\alpha_1$-adrenoreceptor activity in the detrusor, causing frequency and urgency. On these bases, $\alpha_1$-antagonists are used in clinical practice to treat LUTS in women. The results of Serels also indicate that the combined administration of $\alpha_1$-antagonists and anticholinergics can have improved efficacy in treatment of LUTS, as suggested by Fitzpatrick (*International British J. Urol.* 85, Supp. 2: 1–5, 2000).

Another possible use of $\alpha_1$-antagonists is the management of neurogenic lower urinary tract dysfunction (NLUTD), as can be caused by neurological disease or trauma. NLUTD may lead to debilitating symptoms and serious complications, including increased urinary frequency, incontinence, voiding difficulty, recurrent upper urinary tract infections, and upper urinary tract deterioration. Management of NLUTD is indicated to preserve renal function and avoid urological complications. Administration of $\alpha_1$-antagonists may benefit patients with NLUTD by facilitating urine storage by alleviating high detrusor pressure during bladder filling, which is evidenced by poor bladder compliance and detrusor hyperreflexia. In both animal models and patients with spinal cord injury resistant to anticholinergics, $\alpha_1$-antagonists improved bladder compliance. (Serels, ibid.; Fitzpatrick, ibid.; Kakizaki, M. et al., *Brit. J. Urol International* 85, Supp. 2: 25–30, 2000; Sundin, T. et al., *Invest. Urol.* 14: 322–328, 1977; McGuire et al., *Neurology and Urodynamics* 4: 139–142, 1985; Swierzewski, S. J. et al., *J. Urol.* 151: 951–954, 1994).

Two distinct $\alpha_1$-adrenoceptor subtypes have been suggested to be present in the human prostate, one with high ($\alpha_{1H}$) and one with low ($\alpha_{1L}$) affinity for prazosin. All three high-affinity $\alpha_1$-adrenoceptor subtypes found in molecular cloning studies have been identified in prostatic stromal tissue. The $\alpha_{1a}$ subtype was found to be the dominant, representing about 60–85% of the $\alpha_1$-adrenoceptor population. Recent findings suggest that there may be differences in subtype populations between normal and hyperplastic prostates, the ratios between the subtypes $\alpha_{1a}$:$\alpha_{1b}$:$\alpha_{1d}$ being 85:1:14 in BPH tissue and 63:6:31 in non-BPH tissue.

The $\alpha_{1A}$ adrenoceptor was reported to mediate the contractile response of the human prostate in vitro. Ford et al. (*Br. J. Pharmacol.* 114: 24 P, 1995), found that the $\alpha_{1A}$ adrenoceptor may not mediate contractile responses to noradrenaline, and suggested as a candidate the $\alpha_{1L}$ adrenoceptor. Findings by Kenny et al. (*Br. J. Pharmacol.* 118: 871–878, 1996) support the view that the $\alpha_{1L}$ adrenoceptor, which appears to share many of the characteristics of an $\alpha_{1A}$ adrenoceptor, mediates the contractile response of the human prostate.

On the other hand, it has also been suggested that the $\alpha_{1A}$ and $\alpha_{1L}$ adrenoceptors may represent distinct pharmacological forms of the same receptor.

In the female urethra, mRNA for the $\alpha_1$ subtype was predominant and autoradiography confirmed the predominance of the $\alpha_{1A}$ adrenoceptor (Andersson K. E., *Brit. J. Urol. Intl.* 85, Supp. 2: 12–18, 2000). The $\alpha_{1A}$ and $\alpha_{1D}$ subtypes are reported to be present in the human detrusor, with the latter subtype predominant (Malloy B. et al., *J. Urol.* 160: 937–943, 1998). Accordingly, the evidence that $\alpha_1$ adrenoreceptor antagonists are useful in treating lower urinary tract symptoms of both prostatic and non-prostatic origin in both males and females can be used to support the usefulness of the compounds of the present invention in treating such symptoms regardless of whether they are of obstructive origin or not and regardless of the sex of the patient.

The affinity of the compounds of the invention for each receptor can be assessed by receptor binding assays, for example as follows:

(1) $\alpha_1$-adrenergic-receptor subtypes: using the specific ligand $^3$H-prazosin, according to Testa R. et al., *Pharmacol. Comm.* 6: 79–86, 1995; Cotecchia S. et al., *Proc. Natl. Acad. Sci. USA*, 85: 7159–7163, 1988; Furchgott R. E., *Handbook of Experimental Pharmacology—New Series*, 283–335, 1972; Michel M. C. et al., *Brit. J. Pharmacol.* 111: 533–538, 1994; Schwinn D. A. et al., *J. Biol. Chem.* 265: 8183–8189, 1990; Testa R. et al., *Eur. J. Pharmacol.* 249: 307–315, 1993.

(2) $5HT_{1A}$-serotonergic receptors: using the specific ligand $^3$H-8-OH-DPAT according to Fargin et al., *Nature* 335: 358–360, 1988; Kobilka B. K. et al., *Nature* 329: 75–79, 1987; Cullen B. R., *Meth. Enzym.* 152: 684–704, 1987; Gozlan H. et al., *J. Receptor Res.* 7: 195–221, 1987.

The $\alpha_{1L}$ adrenergic receptor is not yet cloned and, therefore, the functional affinity of the compounds of the invention for this subtype can be assessed by using an isolated organ preparation as reported by Testa R. et al. (*J. Pharmacol. Exp. Ther.*, 281, 1284–1293, 1997).

In vitro testing of compounds of this invention on the above receptors is described in Ex.s 26 and 27 below.

The drugs having $\alpha_1$-adrenergic antagonistic activity currently used for the symptomatic therapy of BPH are poorly subtype selective and subject to cause relevant side effects due to their hypotensive activity.

Thus there is still a need for selective a:, antagonists which do not subject the BPH patient to the side effects, especially the cardiovascular side effects, of said treatments. The very high uroselectivity of the compounds of this invention has been tested in the dog model described in Ex. 28, where their efficacy in antagonizing the contractions of prostatic urethra in the presence of very limited effects on blood pressure has been shown, in comparison to Compound A and to other well know ax, antagonists, prazosin and terazosin.

In addition, the longer duration of action of the compounds of the invention has been assessed in the dog model in Ex. 29.

Other features and advantages of the present invention will be apparent to those skilled in the art from the following detailed description and appended claims.

SYNTHESIS OF THE COMPOUNDS OF THE INVENTION

The compounds according to the invention may generally be prepared as follows:

Scheme 1

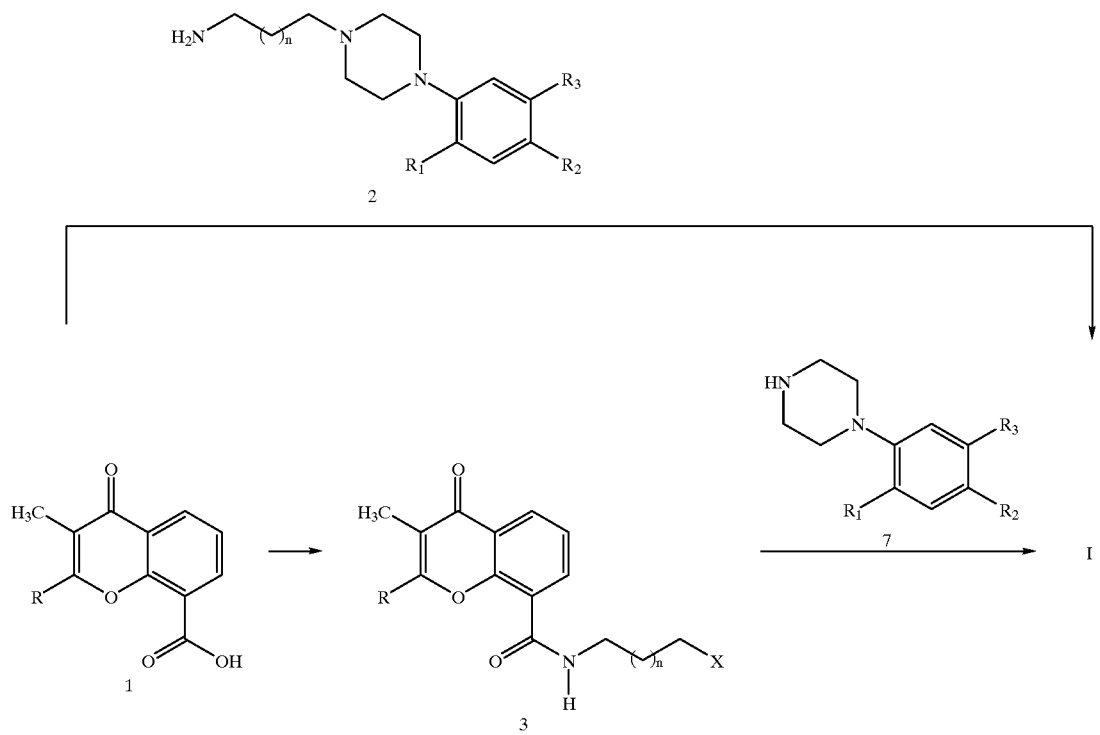

The condensation of acids 1 with ω-aminoalkylamino derivatives 2 (Scheme 1) can be carried out in the presence or absence of a coupling agent (e.g. dicyclohexylcarbodiimide or diethyl cyanophosphonate) optionally in the presence of a promoting agent (e.g. N-hydroxysuccinimide, 4-dimethylaminopyridine or N,N'-carbonyldiimidazole) in a polar aprotic or chlorinated solvent (e.g., dimethylformamide or chloroform) at −10/140° C. (Albertson N. F., *Org. React.* 12: 205–218, 1962; Doherty A. M. et al., *J. Med. Chem.*, 35: 2–14, 1992; Ishihara Y. et al., *Chem. Pharm. Bull.*, 39: 3236–3243, 1991).

In some cases the intermediate esters or amides (such as N-hydroxysuccinimidyl esters or acyl imidazolides) can be isolated and further reacted with 2 to be transformed into the corresponding amides (I) in polar aprotic or chlorinated solvent at 10/100° C. Another intermediate which can be used is the mixed anhydride obtainable by reacting 1 with an alkyl chloroformate in the presence of a tertiary amine (e.g., triethylamine or N-methylmorpholine) followed by addition of 2 at 0–80° C., optionally a promoting agent (e.g., 1-hydroxypiperidine) may be added before the amine addition (Albertson N. F., *Org. React.* 12: 157, 1962).

Alternatively the condensation can be carried out without solvent at 150–220° C. (Mitchell J. A. et al., *J. Am. Chem. Soc.* 53: 1879, 1931) or in high-boiling ethereal solvents (e.g., diglyme). The condensation can also be performed through isolation of reactive derivatives of 1 such as acyl halides. Preparation of acyl halides of compounds of formula 1 and reactions with amines 2 to form amides is well documented in the literature and known to people skilled in the art.

Also less reactive derivatives of 1 can be used, such as alkyl esters, which, in turn, can be converted into I in the presence of a condensing agent (e.g., trimethylaluminium) in an aprotic and/or chlorinated solvent (e.g., hexane, dichloromethane) at −10/80° C., or without solvents at 80–180° C. (Weinreb S. M. et al., *Tetrahedron Lett.* 4171, 1977; Lipton M. F. et al., *Org. Synth.* 59: 49, 1979).

By the same methods of condensation reported above and using $H_2NCH_2(CH_2)_nCH_2X$ (with X=halogen or OH) as a reagent, 1 can be converted into the corresponding derivatives 3. Compounds 3 (with X=leaving group such as halogen, alkylsulphonyloxy or arylsulphonyloxy group) can be subsequently reacted with the appropriate phenylpiperazine 7 directly or by two sequential reactions, in the case of X═OH derivatives, which include conversion of the alcoholic group into a suitable leaving group by methods well known to those skilled in the art. The nucleophilic substitution on 3 to give I is preferably, but not necessarily, carried out at a temperature within the range of 20–160° C. in a polar solvent such as dimethylformamide, acetonitrile, methanol, or without solvent, usually in the presence of a base such as potassium carbonate. See also Gibson's chapter in Patai, *The Chemistry of the Amino Group*, p. 45, Wiley Int. Sci., N.Y., 1968.

The preparation of compounds 2 which are not commercially available is disclosed in the literature and is well known to those skilled in the art and is usually carried out performing nucleophilic substitution of a phenylpiperazine 7 on an N-(ω-haloalkyl)phthalimide or suitable ω-haloalkylnitrile or amide by the method illustrated above. Standard phthalimido-group deprotection and reduction of the amido or cyano group provide compounds 2.

Alternatively, addition of 7 to α,β-unsaturated alkylamides or nitriles (Michael reaction; March J., *Advanced Organic Chemistry*, 4th edition, J. Wiley, ed., page 760, 1992) can be used, followed by reduction of the amido or cyano groups. The addition of α,β-unsaturated alkylamides or nitrile can be carried out in solvents such as ethanol, acetonitrile, toluene, dimethylformamide or a chlorinated solvent at a temperature between 20–25° C. and the reflux temperature in the presence or absence of catalysts such as triethylamine, 4-dimethylaminopyridine.

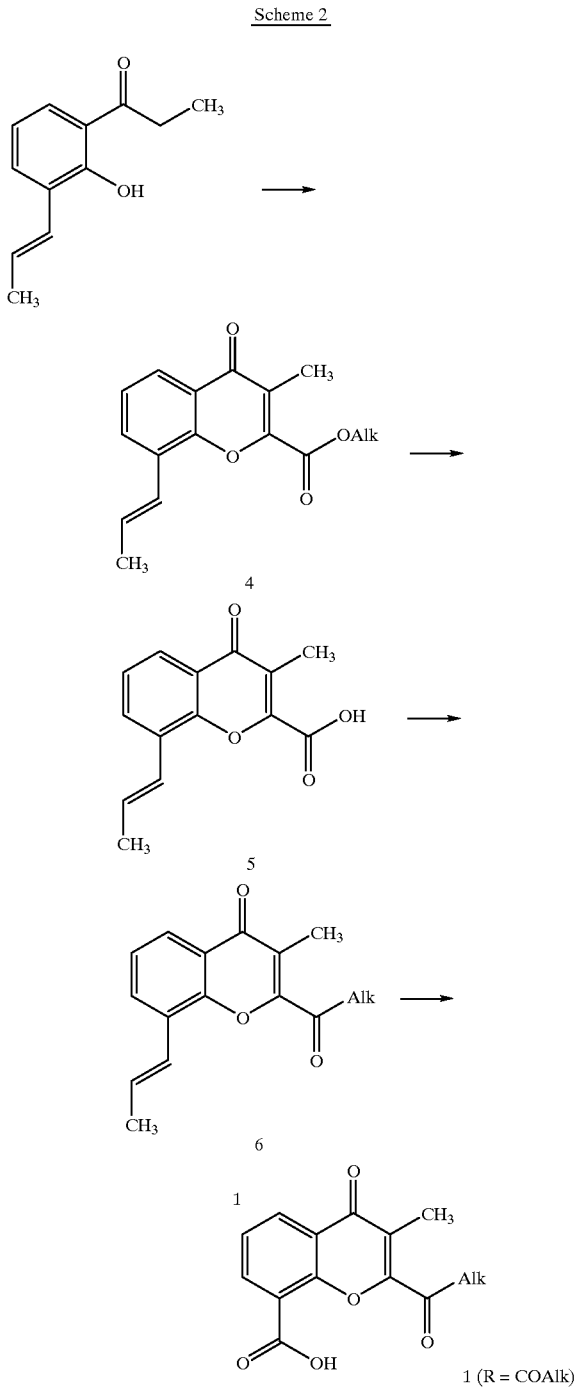

Scheme 2

The compounds 1 of the invention in which R represents an alkylcarbonyl group (Scheme 2) can be synthesized starting from 2-hydroxy-3-(1-propenyl)propiophenone which is condensed with excess diethyl oxalate in the presence of a base (e.g., sodium ethoxide, sodium hydride, sodium metal, lithium or sodium amide, potassium t-butoxide, lithium hexamethyldisilyl azide) in a suitable solvent such as ethanol, toluene, dioxane, tetrahydrofuran, 1,2-dichlorobenzene (or other aprotic solvent) or without any solvent at a temperature in the range between 20° C. and the reflux temperature of the reaction mixture (March J., *Advanced Organic Chemistry*, J. Wiley, Chapter 10, 491–493, 1992; Schmutz, J., *Helvetica Chimica Acta*, 767–779, 1951). The intermediate crude α,γ-diketoester is directly cyclized to 4 (Alk=$C_{1-4}$ alkyl) by acid catalysis using an appropriate acid (e.g., 37% HCl, 98% $H_2SO_4$, glacial acetic acid, trifluoroacetic acid, perchloric acid) in an appropriate solvent such as ethanol, toluene, a chlorinated solvent, or without any solvent, at a temperature in the range between 20° C. and the reflux temperature of the reaction mixture (Bryan J. D., *J. Chem. Soc Perkin Trans.* 1: 1279–1281, 1960). Hydrolysis of the ester function of 4, typically accomplished by acid or base catalysis using methods well known to those skilled in the art, affords Compounds 5. Such procedures include the use of sodium hydroxide in aqueous ethanol at 40–75° C. or lithium hydroxide in aqueous dimethylformamide or dioxane or tetrahydrofuran at 40–100° C.

Compounds 5 can be converted into keto derivatives 6 by direct reaction of lithium carboxylate with alkyl lithium derivatives (Rubottom G. M., *J. Org. Chem.* 48: 1550–1552, 1983). Alternatively, the carboxy group may be converted to keto derivatives by first converting the carboxy group into a more reactive C(O)X group, where X is 1-imidazolyl, chloro or bromo, OC(O)R or other reactive group, and then continuing the reaction with, for example, Meldrum's acid to afford an enolacyl derivative that can be hydrolyzed with acetic acid to give 6 or, alternatively, with the magnesium salt of a suitable β-diester (such as di-t-butyl malonate or diethyl malonate) to afford the corresponding β-ketoester to be hydrolyzed to 6.

Oxidative cleavage of the exocyclic double bond may be accomplished by methods well known to those skilled in the art, as, for example, by permanganate oxidation or other oxidative method (see, for example, Haines A. H., *Methods for the oxidation of organic compounds*, Academic press, 1985, Chapter 3, part 5, 146–151) to yield the desired carboxylic acids 1 having R=C(O)Alk (Alk=$C_{1-4}$ alkyl). Acids 1 in which R is a COOAlk (Alk=$C_{1-4}$ alkyl) group can be clearly prepared from intermediates 4 carrying out the double-bond oxidation step as described above for 6.

Acids 1 in which R is a $CONR_1R_2$ group can be prepared from intermediates 5 through an amidification reaction, which is well known to those skilled in the art, such as that described for 1, with ammonia or an appropriate amine, and oxidation of the double-bond is carried out as described above. A preferred method of amidification under mild conditions includes conversion of 5 to the respective acyl chloride by the use of oxalyl chloride (EP 0625522, Sohda et al.).

Compounds I in which R is a cyano group be obtained from compounds I with R=$CONH_2$ by a dehydration reaction through the use of triphenylphosphine in carbon tetrachloride or toluene or other suitable solvent at room temperature—reflux or, more preferably, by the use of phosphorous-oxychloride/dimethylformamide or by other dehydration methods known to those skilled in the art (March J., *Advanced Organic Chemistry*, J. Wiley, Part 2, Chapter 7, part 39, 1041–1042, 1992).

Compounds I in which R is a NHCOOAlk (Alk=$C_{1-4}$ alkyl) group can be prepared from intermediate 5 by Curtius rearrangement (March J., *Advanced Organic Chemistry*, 4$^{th}$ edition, J. Wiley, ed., pages 1091–1092, 1992) carried out with diphenylphosphoryl azide and triethylamine in an appropriate alkanol at reflux or in a mixture of acetonitrile (or other solvent) and the appropriate alkanol. Oxidation of these intermediates as above affords acids 1 with R=NHCOOAlk (Alk=$C_{1-4}$ alkyl).

Compounds I in which $R_1$ is a trifluoromethanesulphonyloxy group can be synthesized starting from compounds I in which $R_1$ is a hydroxy group by procedures that include the use of trifluoromethanesulphonic anhydride or N-phenyltrifluoromethanesulphonimide in aprotic solvents such as 1,2-dichloroethane or other chlorinated solvents or toluene at a temperature in the range between −20° C. and the reflux temperature of the solvent (Hendickson J. B., *Tetrahedron Letters,* 4607–4610, 1973).

The N-oxides of compounds I can be synthesized by simple oxidation procedures well known to those skilled in the art. The oxidation procedure described by P. Brougham et al. (*Synthesis,* 1015–1017, 1987), allows the two nitrogen of the piperazine ring to be differentiated, enabling both the N-oxides and N,N'-dioxide to be obtained.

The preparation of phenylpiperazines 7 not yet disclosed in the literature is well documented in the experimental part and uses synthetic procedures well known to those skilled in the art, which comprise the synthesis of the proper aniline through well known reactions and the subsequent cyclization with bis-(2-chloroethyl)amine to afford the piperazine following the method of Prelog, *Collect. Czech. Chem. Comm.* 5: 497–502, 1933) or its variations (Elworthy T. R., *J. Med. Chem.* 40: 2674–2687, 1997).

DETAILED SYNTHESIS

Some examples are shown below to illustrate the invention as described in this text, with no intention to limit it.

EXAMPLE 1

2-Carbamoyl-8-{3-[4-(5-chloro-2-methoxyphenyl)-1-piperazinyl]-propylcarbamoyl}-3-methyl-4-oxo-4H-1-benzopyran a) 2-Ethoxycarbonyl-3-methyl-4-oxo-8-(1-propenyl)-4H-1-benzopyran.0.125 $H_2O$ (Compound 1A) 33

A solution of sodium ethoxide prepared from 4.6 g of sodium metal and 100 mL of anhydrous ethanol was added to a solution of 10.0 g of 2-hydroxy-3-(1-propenyl)-propiophenone (prepared as described in Takahaschi T. et al., *J. Pharmacol. Soc. Jpn.* 74, 48 (1954); C.A. 49:1623 (1954)) and 71.2 mL of diethyl oxalate in 160 mL of anhydrous toluene. The resulting solution was stirred at 50° C. for 3.5 hours and cooled to room temperature. Afterwards, 16 mL of 98% sulphuric acid was added dropwise and the resulting mixture was stirred at 50° C. for 0.5 hours. The mixture was cooled to room temperature, diluted with 150 mL of ethyl acetate, washed with water (3×200 mL), dried over anhydrous sodium sulphate and evaporated to dryness under reduced pressure. The crude product was rinsed with 150 mL of diethyl ether and the precipitated solid was removed by filtration to yield 8.82 g (62%) of Compound 1A. M.p. 131–135° C.

| $^1$H-NMR (200 MHz, $CDCl_3$, δ) | | | |
|---|---|---|---|
| 8.01 | dd | 1H | H5 (H7) |
| 7.69 | dd | 1H | H7 (H5) |
| 7.36 | dd | 1H | H6 |
| 6.50–6.91 | m | 2H | CH=CH |
| 4.49 | q | 2H | $CH_2$ |
| 2.39 | s | 3H | $CH_3C$ |
| 2.00 | dd | 3H | $CH_3CH=$ |
| 1.48 | t | 3H | $CH_3CH_2$ | b) 2-Carboxy-3-methyl-4-oxo-8-(1-propenyl)-4H-1-benzopyran (Compound1B)

A solution of 9.03 g of Compound 1A in 110 mL of methanol and 90 mL 1N sodium hydroxide was stirred at room temperature for 3 hours. 100 mL of water was added to the solution and the methanol was removed by evaporation under vacuum. The aqueous solution was kep at 50° C. for 24 h, acidified by 1N HCl and filtered to yield 7.79 g (96%) of Compound1B. M.p. 224–228° C. (ethanol).

| $^1$H-NMR (200 MHz, DMSO-$d_6$, δ) | | | |
|---|---|---|---|
| 13.50–15.00 | br | 1H | COOH |
| 7.80–8.03 | m | 2H | H5 and H7 |
| 7.42 | dd | 1H | H6 |
| 6.55–6.90 | m | 2H | CH=CH |
| 2.24 | s | 3H | $CH_3C$ |
| 1.92 | d | 3H | $CH_3CH=$ | c) trans-2-carbamoyl-3-methyl-4-oxo-8-(1-propenyl)-4H-1-benzopyran (Compound 1C)

0.66 mL of thionyl chloride was added to a solution of 2.0 g of Compound 1B in 30 mL of dichloromethane and 1 mL of dimethylformamide. The solution was stirred at room temperature for 2 hours, and allowed to sit overnight. 0.15 mL of thionyl chloride was added and the solution was stirred at room temperature for 2 hours. The solvent was removed by evaporating under vacuum and the residue was rinsed with dichloromethane (2×30 mL) and evaporated to dryness. The residue was taken up with 30 mL of anhydrous tetrahydrofuran; 5 mL of 32% aqueous ammonia was added, the mixture was stirred at room temperature for 0.5 hours and poured into 200 mL of water. The solution was allowed to sit overnight and the precipitated solid was isolated by filtration to yield 1.11 g (57%) of Compound 1C. M.p. 243–245° C.

| $^1$H-NMR (200 MHz, DMSO-$d_6$, δ) | | | |
|---|---|---|---|
| 8.02–8.20 and 8.20–8.40 | 2 br | 2H | $NH_2$ |
| 7.80–8.00 | m | 2H | H5 and H7 |
| 7.42 | dd | 1H | H6 |
| 6.55 | dq | 1H | $CH_3CH=$ |
| 5.93 | d | 1H | $CH_3CH=CH$ |
| 2.11 | s | 3H | $CH_3C$ |
| 1.94 | d | 3H | $CH_3CH=$ | d) 2-Carbamoyl-8-carboxy-3-methyl-4-oxo-4H-1-benzopyran (Compound 1D)

1.5 mL of an aqueous solution of 70% sodium dichromate and 1.8 mL of 70% sulphuric acid were added to a solution of 0.6 g of Compound 1C in 30 mL of acetone and 10 mL of dimethylformamide. The solution was stirred for 4 hours at 50° C. Additional 3 mL of 70% sodium dichromate and 3.6 mL of 70% sulphuric acid in total were added in 2 steps after 6 hours at 50° C. and after 6 hours at 70° C, respectively. The solution was stirred at 70° C. for 6 hours, cooled to room temperature, poured into a solution of 1 g of sodium dithionite in 100 mL of water, stirred for 0.5 hours and filtered after 12 hours at 5° C. to give 0.47 g (83%) of Compound 1D. M.p.>250° C.

| $^1$H-NMR (200 MHz, DMSO-$d_6$, δ) | | | |
|---|---|---|---|
| 13.0–14.0 | br | 1H | COOH |
| 8.15–8.42 | m | 3H | H5, H7 and CON$\underline{H}$H |
| 7.80 | bs | 1H | CONH$\underline{H}$ |
| 7.55 | dd | 1H | H6 |
| 2.24 | s | 3H | $CH_3$ | e) 1-(5-Chloro-2-methoxyphenyl)-4-[3-(N-phthalimido) propyl]piperazine (Compound 1E)

A mixture of 28.64 g of 1-(5-chloro-2-methoxyphenyl) piperazine, 44.6 g of anhydrous potassium carbonate and 33.65 g of N-(3-bromopropyl)phthalimide in 250 mL of acetonitrile was stirred at reflux for 8 hours. After cooling to room temperature, 800 mL of water was added with stirring and the resulting suspension was filtered by suction yielding a yellowish solid. This was washed with 300 mL of water and crystallized from methanol to yield 46.5 g (91%) of the title compound, melting at 131–133° C.

| $^1$H-NMR (200 MHz, $CDCl_3$, δ) | | | |
|---|---|---|---|
| 7.78–7.82 | m | 2H | phthalimide H3 and H6 |
| 7.64–7.78 | m | 2H | phthalimide H4 and H5 |
| 6.92 | dd | 1H | methoxyphenyl H4 |
| 6.65–6.78 | m | 2H | methoxyphenyl H3 and H6 |
| 3.81 | s | 3H | $CH_3O$ |
| 3.71–3.89 | m | 2H | $CH_2N(CO)_2$ |
| 2.78–3.00 | m | 4H | 2 piperazine $CH_2$s |
| 2.40–2.65 | m | 6H | 2 piperazine $CH_2$s, $C\underline{H}_2CH_2CH_2N(CO)_2$ |
| 1.80–2.03 | m | 2H | $CH_2C\underline{H}_2CH_2$ | f) 1-(3-Aminopropyl)-4-(5-chloro-2-methoxyphenyl) piperazine trihydrochloride.2.15 $H_2O$ (Compound 1F)

A solution of 20.7 g of Compound 1E and 8.6 mL of 85% hydrazine hydrate in 300 mL of ethanol was stirred at reflux for 3.5 hours. Afterwards, the reaction mixture was cooled to room temperature, diluted with 400 mL of water, acidified with 37% hydrochloric acid (pH=1) and stirred for 0.5 hours. The precipitated solid was collected by filtration and washed with 1N hydrochloric acid followed by water. The filtrate was concentrated by evaporation in vacuo, filtered, made basic by addition of 35% sodium hydroxide at 0–5° C. and extracted with diethyl ether. The organic layer was washed with brine, dried over sodium sulphate and evaporated to dryness in vacuo affording 13.6 g (96%) of the title compound as a base. Acidification of a solution of the base in chloroform with more than three equivalents of anhydrous 3N ethanolic hydrogen chloride, followed by evaporation to dryness in vacuo and crystallisation of the residue from ethanol/diethyl-ether 10:3, yielded the title compound, melting at 200–202° C.

| $^1$H-NMR (200 MHz, DMSO-$d_6$, δ) | | | |
|---|---|---|---|
| 11.20–11.50 | bs | 1H | $NH^+$ |
| 8.10–8.40 | bs | 3H | $NH_3^+$ |
| 6.85–7.10 | m | 3H | H3, H4 and H6 of phenyl ring |
| 5.10 | bs | 5.3H | $NH^+$, 2.15 $H_2O$ |
| 3.79 | s | 3H | $CH_3O$ |
| 3.35–3.65 | m | 4H | 2 piperazine $CH_2$s |
| 3.03–3.35 | m | 6H | 2 piperazine $CH_2$s, $CH_2CH_2C\underline{H}_2NH_2$ |
| 2.80–3.03 | m | 2H | $C\underline{H}_2CH_2CH_2NH_2$ |
| 1.95–2.22 | m | 2H | $CH_2C\underline{H}_2CH_2NH_2$ | g) 2-Carbamoyl-8-{3-[4-(5-chloro-2-methoxyphenyl)-1-piperazinyl]-propylcarbamoyl}3- methyl-4-oxo-4H-1-benzopyran 0.35 mL of 93% diethyl cyanophosphonate and 0.30 mL of triethylamine were added to a solution of 0.45 g of Compound 1D and 0.60 g of Compound 1F in 30 mL of anhydrous dimethylformamide at 0° C. The mixture was stirred for 4 hours between 0° C. and 25° C., then poured into 200 mL of water and filtered after overnight resting at 5° C. The filtered solid was purified by crystallisation from acetonitrile affording 0.69 g (69%) of the title compound. M.p. 184–192° C.

| $^1$H-NMR (200 MHz, $CDCl_3$, δ) | | | |
|---|---|---|---|
| 8.58 | ta | 1H | CONH |
| 8.31 | dd | 1H | H5 (H7) |
| 7.92 | dd | 1H | H7 (H5) |
| 7.65 | bs | 1H | CON$\underline{H}$H |
| 7.40 | dd | 1H | H6 |
| 6.94 | dd | 1H | phenyl H4 |
| 6.68–6.80 | m | 2H | phenyl H3 and H6 |
| 5.75 | bs | 1H | CONH$\underline{H}$ |
| 3.82 | s | 3H | $CH_3O$ |
| 2.63 | dt | 2H | $NHC\underline{H}_2CH_2CH_2N$ |
| 2.83–3.00 | m | 4H | 2 piperazine $CH_2$s |
| 2.58–2.80 | m | 6H | 2 piperazine $CH_2$s, $CH_2CH_2C\underline{H}_2NH_2$ |
| 2.50 | s | 3H | $CH_3C$ |
| 1.86 | tt | 2H | $NHCH_2C\underline{H}_2CH_2N$ |

EXAMPLE 2

2-Acetyl-8-{3-[4-(5-chloro-2-methoxyphenyl)-1-piperazinyl]propylcarbamoyl}-3-methyl-4-oxo-4H-1-benzopyran a) 2-Chlorocarbonyl-3-methyl-4-oxo-8-(1-propenyl)-4H-1-benzopyran (Compound 2A)

0.31 mL of thionyl chloride was added to a solution of 0.42 g of Compound 1B in 20 mL of anhydrous 1,2-dichloroethane and 3 mL of anhydrous dimethylformamide. The solution was stirred at 60° C. for 2 hours. The solvents were evaporated off under vacuum and the residue was taken up with toluene (2×30 mL). Evaporation to dryness gave crude compound 2A, used in the next step without further purification.

b) 2-Acetyl-3-methyl-4-oxo-8-(1-propenyl)-4H-1-benzopyran (Compound 2B)

0.051 g of magnesium turnings were suspended in 10 mL of anhydrous ethanol. 0.3 mL of carbon tetrachloride and 0.32 mL of diethyl malonate were added and the resulting mixture was stirred at room temperature (with spontaneous heating) for 1 hour, then at 60° C. for 2 hours and cooled to room temperature. A solution of 0.42 g of Compound 2A in 15 mL of toluene and chloroform (5 mL) was added dropwise and the resulting mixture was stirred at room temperature for 6 hours. After overnight resting, 0.12 mL of 98% sulphuric acid and 3 mL of water were added; the precipitated inorganic salts were filtered off and the filtrate was evaporated under vacuum to dryness.

The residue was rinsed with mL of glacial acetic acid, 0.5 mL of 98% sulphuric acid and 3 mL of water and stirred at reflux for 2 hours. After cooling to room temperature, the solution was poured into water (200 mL), alkalinised with 35% sodium hydroxide and extracted with chloroform (3×80 mL). The combined organic phases were dried over sodium sulphate and the solvents were evaporated off under vacuum. The crude was purified by flash chromatography (ethyl acetate/petroleum ether 1:9) to give 0.21 g (48%) of Compound 2B.

| $^1$H-NMR (200 MHz, CDCl$_3$, δ) | | | |
|---|---|---|---|
| 8.05 | dd | 1H | H5 (H7) |
| 7.79 | dd | 1H | H7 (H5) |
| 7.38 | dd | 1H | H6 |
| 6.85 | bd | 1H | CH$_3$CH=C$\underline{\text{H}}$ |
| 6.45 | dq | 1H | CH$_3$C$\underline{\text{H}}$=CH |
| 2.70 | s | 3H | CH$_3$CO |
| 2.37 | s | 3H | CH$_3$C |
| 2.00 | dd | 3H | C$\underline{\text{H}}_3$CH=CH | c) 2-Acetyl-8-carboxy-3-methyl-4-oxo-4H-1-benzopyran (Compound 2C)

1.2 mL of 70% sulphuric acid and 1 mL of 70% aqueous sodium dichromate were added to a solution of 0.21 g of Compound 2B in 10 mL of acetone. The resulting solution was stirred at room temperature for 2 hours. 10 mL of 10% sodium dithionite was added and the mixture was stirred at room temperature for 0.5 hours. The organic solvent was evaporated off under vacuum, 50 mL of water was added and the precipitated solid was filtered to give 0.15 g (75%) of Compound 2C.

| $^1$H-NMR (200 MHz, CDCl$_3$, δ) | | | |
|---|---|---|---|
| 8.41–8.60 | m | 1H | H5 and H7 |
| 7.53 | dd | 1H | H6 |
| 2.76 | s | 3H | CH$_3$CO |
| 2.40 | s | 3H | CH$_3$C |

Note: The COOH signal cannot be resolved.

d) 2-Acetyl-8-{3-[4-(5-chloro-2-methoxyphenyl)-1-piperazinyl]propylcarbamoyl}-3-methyl-4-oxo-4H-1-benzopyran The title compound was prepared according to the method described in Ex. 1g) but using Compound 2C instead of Compound 1D. The reaction mixture was poured into water and extracted with ethyl acetate (3×50 mL). The organic layer was washed with water, dried over sodium sulphate and the solvents were evaporated off under vacuum to dryness. The crude was purified by flash chromatography (chloroform: methanol 97:3) followed by crystallisation from toluene to afford the title compound (52%).

| $^1$H-NMR (200 MHz, CDCl$_3$, δ) | | | |
|---|---|---|---|
| 8.31 | dd | 1H | H5 (H7) |
| 8.18 | bt | 1H | H7 (H5) |
| 8.10 | dd | 1H | NH |
| 7.46 | dd | 1H | H6 |
| 6.95 | dd | 1H | phenyl H4 |
| 6.73 | d | 1H | phenyl H3 |
| 6.67 | d | 1H | phenyl H6 |
| 3.83 | s | 3H | CH$_3$O |
| 3.68 | dt | 2H | NHC$\underline{\text{H}}_2$CH$_2$CH$_2$N |
| 2.75–3.03 | m | 4H | 2 piperazine CH$_2$s |
| 2.70 | s | 3H | CH$_3$CO |
| 2.60–2.70 | m | 6H | 2 piperazine CH$_2$s and NHCH$_2$CH$_2$C$\underline{\text{H}}_2$N |
| 2.49 | s | 3H | CH$_3$C |
| 1.88 | tt | 2H | NHCH$_2$C$\underline{\text{H}}_2$CH$_2$N |

EXAMPLE 3

2-(1,1-Dimethylethoxycarbonylamino)-8-{3-[4-(5-chloro-2-methoxyphenyl)-1-piperazinyl] propylcarbamoyl}-3-methyl-4-oxo-4H-1-benzopyran monohydrate a) 2-(1,1-Dimethylethoxycarbonylamino)-3-methyl-4-oxo-8-(1-propenyl)-4H-1-benzopyran (Compound 3A)

A solution of 1.5 g of Compound 1B, 1.57 mL of diphenylphosphoryl azide and 1.02 mL of triethylamine in 30 mL of t-butanol was stirred at reflux for 7 hours, cooled to room temperature, poured into 200 mL of water and extracted with ethyl acetate (2×150 mL). The collected organic layers were washed with water and 1N sodium hydroxide, dried over sodium sulphate and evaporated under vacuum. The crude was purified by flash chromatography (ethyl acetate/petroleum ether 3:7) to afford 1.6 g (60%) of Compound 3A. M.p. 200–203° C. (toluene).

| $^1$H-NMR (200 MHz, CDCl$_3$, δ) | | | |
|---|---|---|---|
| 8.05 | d | 1H | H5 (H7) |
| 7.72 | d | 1H | H7 (H5) |
| 7.30 | dd | 1H | H6 |
| 6.75–7.02 | m | 1H | CH$_3$CH=C$\underline{\text{H}}$ |
| 6.60 | bs | 1H | NH |
| 6.42 | dq | 1H | CH$_3$C$\underline{\text{H}}$=CH |
| 2.04 | s | 3H | benzopyran CH$_3$ |
| 1.95 | dd | 3H | C$\underline{\text{H}}_3$CH=CH |
| 1.56 | s | 9H | (CH$_3$)$_3$C | b) 8-Carboxy-2-(1,1-dimethylethoxycarbonylamino)-3-methyl-4H-1-benzopyran (Compound 3B)

The title compound was synthesised following the procedure described for Compound 2C, except that Compound 3A was used instead of Compound 2B. The reaction was carried out at 40° C. Treatment of the reaction mixture with sodium dithionite and extraction with chloroform afforded a crude which was rinsed with 50 mL of ethyl acetate, boiled for 2 hours and filtered to give a first crop of Compound 3B. The mother liquor was evaporated and the residue was purified by flash chromatography (ethyl acetate/petroleum ether/glacial acetic acid 50:50:1) to give a second crop of Compound 3B. Total yield: 34%.

| ¹H-NMR (200 MHz, DMSO-d₆, δ) | | | |
|---|---|---|---|
| 13.40 | bs | 1H | COOH |
| 10.10 | bs | 1H | NH |
| 8.23 | dd | 1H | H5 (H7) |
| 8.15 | dd | 1H | H7 (H5) |
| 7.50 | dd | 1H | H6 |
| 1.89 | s | 3H | $CH_3$ |
| 1.46 | s | 9H | $(CH_3)_3C$ | c) 2-(1,1-dimethylethoxycarbonylamino)-8-{3-[4-(5-chloro-2-methoxyphenyl)-1-piperazinyl] propylcarbamoyl}-3-methyl-4-oxo-4H-1-benzopyran monohydrate The title Compound was prepared following the procedure described in Ex. 1g), but using Compound 3B instead of Compound 1D. The precipitated solid was purified by flash chromatography (ethyl acetate/2N ammonia solution in methanol 97:3) followed by crystallisation from ethyl acetate to afford the title compound (38%). M.p. 177–179° C.

| ¹H-NMR (200 MHz, DMSO-d₆, δ) | | | |
|---|---|---|---|
| 10.40 | bs | 1H | OCONH |
| 8.65 | bt | 1H | CONH |
| 8.10–8.25 | m | 2H | H7 and H5 |
| 7.50 | dd | 1H | H6 |
| 6.90–6.98 | m | 2H | phenyl H3 and H6 |
| 6.73–6.80 | m | 1H | phenyl H4 |
| 3.75 | s | 3H | $CH_3O$ |
| 3.25–3.50 | m | 4H | $NHC\underline{H}_2CH_2CH_2N$ and $H_2O$ |
| 2.85–3.05 | m | 4H | piperazine $CH_2$s at position 3 and 5 |
| 2.30–2.68 | m | 6H | Piperazine $CH_2$s at position 2 and 6, $NHCH_2CH_2C\underline{H}_2N$ |
| 1.90 | s | 3H | $CH_3C$ |
| 1.75 | tt | 2H | $NHCH_2C\underline{H}_2CH_2N$ |
| 1.51 | s | 9H | $(CH_3)_3C$ |

EXAMPLE 4

2-Ethoxycarbonyl-8-{3-[4-(5-chloro-2-methoxyphenyl)-1-piperazinyl]-propylcarbamoyl}-3-methyl-4-oxo-4H-1-benzopyran a) 8-Carboxy-2-ethoxycarbonyl-3-methyl-4-oxo-4H-1-benzopyran (Compound 4A)

The title compound was synthesised following the procedure described for Compound 2C, except that Compound 1A was used instead of Compound 2B. The reaction was carried out at 60° C. for 6 hours. After the usual work-up procedure with sodium dithionite, extraction with ethyl acetate gave a crude which was purified by flash chromatography (ethyl acetate/petroleum ether/glacial acetic acid, gradient from 20:80:1 to 50:50:1) affording Compound 4A (73%) used in the next step without further purification. M.p. 176–179° C. (ethyl acetate/petroleum ether).

| ¹H-NMR (200 MHz, CDCl₃, δ) | | | |
|---|---|---|---|
| 9.5–11.5 | br | 1H | COOH |
| 8.42–8.53 | m | 2H | H5 and H7 |
| 7.53 | dd | 1H | H6 |
| 4.48 | q | 2H | $CH_2$ |
| 2.44 | s | 3H | $CH_3C$ |
| 1.48 | t | 3H | $C\underline{H}_3CH_2$ | b) 2-Ethoxycarbonyl-8-{3-[4-(5-chloro-2-methoxyphenyl)-1-piperazinyl]-propylcarbamoyl}-3-methyl-4-oxo-4H-1-benzopyran The title compound was prepared following the procedure described in Ex. 1g), but using Compound 4A instead of Compound 1D. Extraction with ethyl acetate gave a crude which was purified by flash chromatography (ethyl acetate/methanol 98:2) followed by crystallisation from ethyl acetate affording the title compound (46%). M.p. 107–115° C.

| ¹H-NMR (200 MHz, CDCl₃, δ) | | | |
|---|---|---|---|
| 8.63 | dd | 1H | H5 (H7) |
| 8.34 | dd | 1H | H7 (H5) |
| 7.52 | dd | 1H | H6 |
| 6.91 | dd | 1H | phenyl H4 |
| 6.82 | d | 1H | phenyl H6 |
| 6.76 | d | 1H | phenyl H3 |
| 4.53 | q | 2H | $CH_3C\underline{H}_2$ |
| 3.83 | s | 3H | $CH_3O$ |
| 3.64 | t | 2H | $NHC\underline{H}_2CH_2CH_2N$ |
| 2.95–3.14 | m | 4H | 2 piperazine $CH_2$s |
| 2.60–2.78 | m | 4H | 2 piperazine $CH_2$s |
| 2.55 | t | 2H | $NHCH_2CH_2C\underline{H}_2N$ |
| 2.45 | s | 3H | $CH_3C$ |
| 1.95 | tt | 2H | $NHCH_2C\underline{H}_2CH_2N$ |
| 1.49 | t | 3H | $C\underline{H}_3CH_2$ |

EXAMPLE 5

8-{3-[4-(5-Chloro-2-methoxyphenyl)-1-piperazinyl] propylcarbamoyl}-3-methyl-2-methylcarbamoyl-4-oxo-4H-1-benzopyran a) 3-Methyl-2-methylcarbamoyl-8-(1-propenyl)-4-oxo-4H-1-benzopyran (Compound 5A)

0.29 mL of oxalyl chloride was added to a mixture of 0.5 g of Compound 1B in 10 mL of anhydrous toluene and 1 mL of anhydrous dimethylformamide at room temperature. The resulting mixture was stirred at 40° C. for 2 hours and at room temperature for 3hours. It was then cooled to 0° C. and 2.0 mL of a 3M solution of methylamine in toluene was added. The solution was stirred at 0° C. –25° C. for 8 hours. The reaction mixture was evaporated to dryness. The residue was rinsed with 50 mL of ethyl acetate and 5 mL of methanol and washed with water, and the solvent was evaporated off under vacuum. The crude was taken up with 10 mL of ethyl acetate, boiled for 1 hour, and filtered after overnight resting at 5° C. to give 0.35 g (66%) of Compound 5A.

| ¹H-NMR (200 MHz, CDCl₃, δ) | | | |
|---|---|---|---|
| 8.10 | d | 1H | H5 (H7) |
| 7.75 | d | 1H | H7 (H5) |
| 7.35 | dd | 1H | H6 |
| 6.71–6.89 | m | 2H | $CH_3CH=CH$ and NH |
| 6.40 | dq | 1H | $CH_3C\underline{H}=CH$ |

¹H-NMR (200 MHz, CDCl₃, δ)

| | | | |
|---|---|---|---|
| 3.12 | d | 3H | CH₃N |
| 2.42 | s | 3H | CH₃C |
| 2.00 | d | 3H | C$\underline{H}$₃CH=CH | b) 8-Carboxy-3-methyl-2-methylaminocarbonyl-4-oxo-4H-1-benzopyran (Compound 5B)

The title compound was prepared following the method described for Compound 2C but using Compound 5A instead of Compound 2B. The reaction mixture was poured into an 1% aqueous solution of sodium dithionite and filtered after overnight resting to give Compound 5B (60%).

¹H-NMR (200 MHz, DMSO-d₆, δ)

| | | | |
|---|---|---|---|
| 13.60 | bs | 1H | COOH |
| 8.50 | bd | 1H | NH |
| 8.20–8.35 | m | 2H | H5 and H7 |
| 7.55 | dd | 1H | H6 |
| 2.85 | d | 3H | CH₃N |
| 2.15 | s | 3H | CH₃C | c) 8-{3-[4-(5-Chloro-2-methoxyphenyl)-1-piperazinyl]propylcarbamoyl}-3-methyl-2-methylcarbamoyl-4-oxo-4H-1-benzopyran The title compound was prepared according to the method described in Ex. 1g but using Compound 5B instead of Compound 1D. The reaction mixture was poured into water and filtered after overnight resting at 5° C. The crude was purified by crystallisation from acetonitrile to afford the title compound (70%). M.p. 212–215° C.

¹H-NMR (200 MHz, CDCl₃, δ)

| | | | |
|---|---|---|---|
| 8.60–8.75 | m | 1H | CONH |
| 8.35 | dd | 1H | H5 (H7) |
| 7.98 | dd | 1H | H7 (H5) |
| 7.70–7.75 | m | 1H | CONH |
| 7.40 | dd | 1H | H6 |
| 6.95 | dd | 1H | Phenyl H4 |
| 6.80–6.94 | m | 2H | Phenyl H3 and H6 |
| 3.90 | s | 3H | CH₃O |
| 3.65 | dt | 2H | NHC$\underline{H}$₂CH₂CH₂N |
| 3.09 | d | 3H | C$\underline{H}$₃NH |
| 2.85–3.02 | m | 4H | 2 piperazine CH₂s |
| 2.60–2.82 | m | 6H | 2 piperazine CH₂s and NHCH₂CH₂C$\underline{H}$₂N |
| 2.40 | s | 3H | CH₃C |
| 1.75–1.98 | m | 2H | NHCH₂C$\underline{H}$₂CH₂N |

EXAMPLE 6

8-{3-[4-(5-Chloro-2-methoxyphenyl)-1-piperazinyl]propylcarbamoyl}-3-methyl-2-dimethylcarbamoyl-4-oxo-4H-1-benzopyran a) 2-Dimethylcarbamoyl-3-methyl-8-(1-propenyl)-4-oxo-4H-1-benzopyran (Compound 6A)

0.20 mL of oxalyl chloride was added to a mixture of 0.35 g of Compound 1B in 7 mL of anhydrous toluene and 1 mL of anhydrous dimethylformamide at room temperature. The resulting mixture was stirred at 50° C. for 2 hours and then cooled to 0° C. 1.43 mL of a 2M solution of dimethylamine in toluene was added and the solution was stirred at room temperature for 2 hours. The solvents were evaporated off, the residue was rinsed with 30 mL of ethyl acetate, washed with water and dried over sodium sulphate, and the solvent was evaporated off under vacuum. The crude was taken up with 30 mL of cyclohexane and filtered to give 0.36 g (92%) of Compound 6A.

¹H-NMR (200 MHz, CDCl₃, δ)

| | | | |
|---|---|---|---|
| 8.09 | d | 1H | H5 (H7) |
| 7.75 | d | 1H | H7 (H5) |
| 7.35 | dd | 1H | H6 |
| 6.70–6.90 | m | 1H | CH₃CH=C$\underline{H}$ |
| 6.38 | dq | 1H | CH₃C$\underline{H}$=CH |
| 3.05 and 3.20 | 2s | 6H | (CH₃)₂N |
| 2.10 | s | 3H | CH₃C |
| 1.98 | dd | 3H | CH₃CH=CH | b) 8-Carboxy-2-dimethylcarbamoyl-3-methyl-4-oxo-4H-1-benzopyran (Compound 6B)

The title compound was prepared following the procedure described in Ex. 2c but using Compound 6A instead of Compound 2B. Extraction with dichloromethane, drying over sodium sulphate and evaporation to dryness in vacuo afforded Compound 6B (50%).

¹H-NMR (200 MHz, DMSO-d₆, δ)

| | | | |
|---|---|---|---|
| 13.40 | bs | 1H | COOH |
| 8.20–8.35 | m | 2H | H5 and H7 |
| 7.55 | dd | 1H | H6 |
| 3.02 and 3.10 | 2s | 6H | (CH₃)₂N |
| 1.90 | s | 3H | CH₃C | c) 8-{3-[4-(5-Chloro-2-methoxyphenyl)-1-piperazinyl]propylcarbamoyl}-3-methyl-2-dimethylcarbamoyl-4-oxo-4H-1-benzopyran The title compound was prepared according to the method described in Ex. 1 g but using Compound 6B instead of Compound 1D. Extraction with ethyl acetate afforded a crude which was purified by crystallisation from ethyl acetate (yield 51%). M.p. 151–153° C.

¹H-NMR (200 MHz, CDCl₃, δ)

| | | | |
|---|---|---|---|
| 8.35 | dd | 1H | H5 (H7) |
| 8.16 | dd | 1H | H7 (H5) |
| 7.78 | bt | 1H | NH |
| 7.48 | dd | 1H | H6 |
| 6.95 | dd | 1H | phenyl H4 |
| 6.80–6.84 | m | 2H | phenyl H3 and H6 |
| 3.90 | s | 3H | CH₃O |
| 3.60 | dt | 3H | NHC$\underline{H}$₂CH₂CH₂N |
| 3.06 and 3.18 | 2s | 6H | (CH₃)₂N |
| 2.85–3.02 | m | 4H | 2 piperazine CH₂s |
| 2.50–2.72 | m | 6H | 2 piperazine CH₂s and NHCH₂CH₂C$\underline{H}$₂N |
| 2.10 | s | 3H | CH₃C |
| 1.82–1.92 | m | 3H | NHCH₂C$\underline{H}$₂CH₂N |

EXAMPLE 7

2-Carbamoyl-8-<3-{4-[4-fluoro-2-(2,2,2-trifluoroethoxy)phenyl]-1-piperazinyl}-propylcarbamoyl>-3-methyl-4-oxo-4H-1-benzopyran a) 2-Carbamoyl-8-(3-chloropropylcarbamoyl)-3-methyl-4-oxo-4H-1-benzopyran Compound 7A)

0.66 g of 3-chloropropylamine hydrochloride, 0.86 mL of 92% diethyl cyanophosphonate and 1.42 mL of triethylamine were added to a solution of 1.14 g of Compound 1D in 90 mL of anhydrous dimethylformamide at 0° C. The resulting solution was stirred at room temperature for 2 hours and, after standing overnight, was poured into water. The precipitated solid was collected by filtration after 16 hours standing at 5° C. to afford 1.25 g (85%) of Compound 7A

| $^1$H-NMR (200 MHz, DMSO-d$_6$, δ) | | | |
|---|---|---|---|
| 8.55 | t | 1H | CONH |
| 8.13 | dd | 1H | H5 (H7) |
| 8.02 | bs | 1H | CONHH |
| 7.98 | dd | 1H | H7 (H5) |
| 7.85 | bs | 1H | CONHH |
| 7.47 | dd | 1H | H6 |
| 3.67 | t | 2H | CH$_2$Cl |
| 3.44 | dt | 2H | NHCH$_2$ |
| 2.18 | s | 3H | CH$_3$C |
| 2.01 | tt | 2H | CH$_2$CH$_2$CH$_2$ | b) 2-Carbamoyl-8-<3-{4-[4-fluoro-2-(2,2,2-trifluoroethoxy)phenyl]-1-piperazinyl}-propylcarbamoyl>-3-methyl-4-oxo-4H-1-benzopyran A finely triturated mixture of 0.34 g of 1-[4-fluoro-2-(2,2,2-trifluoroethoxy)phenyl]-piperazine (prepared as described in European Patent EP 748800), 0.39 g of Compound 7A and 0.17 g of anhydrous potassium carbonate was heated at 205° C. for 20 minutes. The reaction mixture was cooled to room temperature, taken up in 100 mL of chloroform and washed with water (2×100 mL). The organic phase was dried over sodium sulphate and the solvent was evaporated off in vacuo. The crude was purified by flash chromatography, eluting with ethyl acetate/2N ammonia solution in methanol 95:5, followed by crystallisation from ethyl acetate to afford 0.21 g (31%) of the title compound. M.p. 195–196° C.

| $^1$H-NMR (200 MHz, CDCl$_3$, δ) | | | |
|---|---|---|---|
| 8.60 | bt | 1H | CONH |
| 8.30 | dd | 1H | H5 (H7) |
| 8.02–8.15 | m | 1H | H7 (H5) |
| 7.75 | bs | 1H | CONHH |
| 7.40 | dd | 1H | H6 |
| 6.70–6.83 | m | 2H | phenyl H3 and H6 (H5) |
| 6.59 | dd | 1H | phenyl H5 (H6) |
| 5.80 | bs | 1H | CONHH |
| 4.35 | q | 2H | OCH$_2$CF$_3$ |
| 3.58–3.75 | m | 2H | NHCH$_2$CH$_2$CH$_2$N |
| 2.70–3.30 | m | 10H | piperazine CH$_2$s and NHCH$_2$CH$_2$CH$_2$N |
| 2.45 | s | 3H | CH$_3$C |
| 1.90–2.10 | m | 2H | NHCH$_2$CH$_2$CH$_2$N |

EXAMPLE 8

2-Carbamoyl-8-<3-{4-[5-fluoro-2-(2,2,2-trifluoroethoxy)phenyl]-1-piperazinyl}-propylcarbamoyl>-3-methyl-4-oxo-4H-1-benzopyran a) 5-Fluoro-2-(2,2,2-trifluoroethoxy)nitrobenzene (Compound 8A)

A stirred mixture of 3.14 g of 4-fluoro-2-nitrophenol, 13 g of cesium carbonate and 20 mL of anhydrous dimethylformamide was heated at 100° C. for 4 hours. 6.65 g of 2,2,2-trifluoroethyl p-toluenesulphonate was then added and the mixture was stirred at the same temperature for 40 hours. The solvent was removed under reduced pressure, and 50 mL of water was added to the residue. The mixture was acidified with 37% hydrochloric acid and extracted with 3×40 mL of ethyl acetate. The organic layer was washed with 20 mL of brine, dried over sodium sulphate and evaporated to dryness under reduced pressure. The residue was purified by flash chromatography (petroleum ether/ethyl acetate 100:7) to afford 1.53 g (32%) of Compound 8A as an oil.

| $^1$H-NMR (200 MHz, CDCl$_3$, δ) | | | |
|---|---|---|---|
| 7.65 | dd | 1H | H6 |
| 7.32 | dd | 1H | H4 |
| 7.16 | dd | 1H | H3 |
| 4.42 | q | 2H | CH$_2$ | b) 5-Fluoro-2-(2,2.2-trifluoroethoxy)aniline (Compound 8B)

A mixture of 0.66 g of Compound 8A and 0.07 g of Raney-Nickel in 20 mL of ethyl acetate was stirred for 14 hours at 20–25° C. The catalyst was filtered off. The mixture was diluted with water. The organic layer was separated and the mixture extracted with 2×40 mL of ethyl acetate. The combined organic layers were washed with 20 mL of brine, dried over sodium sulphate and evaporated to dryness in vacuo to afford 0.52 g (90.6%) of Compound 8B as an oil.

| $^1$H-NMR (200 MHz, CDCl$_3$, δ) | | | |
|---|---|---|---|
| 6.70 | dd | 1H | H6 |
| 6.28–6.50 | m | 2H | H3 and H4 |
| 4.32 | q | 2H | CH$_2$ |
| 3.92 | bs | 2H | NH$_2$ | c) 1-[5-Fluoro-2-(2,2,2-trifluoroethoxy)phenyl]piperazine (Compound 8C)

A stirred mixture of 0.52 g of Compound 8B, 0.45 g of 98% bis-(2-chloroethyl)amine hydrochloride, 0.5 g of potassium iodide, 0.34 g of anhydrous potassium carbonate and 20 mL of n-butanol was refluxed for 32 hours under nitrogen. The solvent was removed under reduced pressure; the residue was treated with 10 mL of water and 10 mL of 20% aqueous sodium carbonate and extracted with 2×30 mL of ethyl acetate. The organic layer was washed with brine, dried over sodium sulphate and evaporated to dryness in vacuo. The residue was purified by flash chromatography (chloroform/2N ammonia solution in methanol, gradient from 100:3 to 100:5) to afford 0.1 g (14%) of Compound 8C as an oil.

| ¹H-NMR (200 MHz, CDCl₃, δ) | | | |
|---|---|---|---|
| 6.80–6.93 | m | 1H | H3 |
| 6.55–6.71 | m | 2H | H6, 4 |
| 4.36 | q | 2H | CH₂CF₃ |
| 3.05 | s | 8H | piperazine CH₂s |
| 2.38 | s | 1H | NH | d) 2-Carbamoyl-8-<3-{4-[5-fluoro-2-(2,2,2-trifluoroethoxy)phenyl]-1-piperazinyl}-propylcarbamoyl>-3-methyl-4-oxo-4H-1-benzopyran This compound was prepared as described in Ex. 7b, with the exception that Compound 8C was substituted for 1-[4-fluoro-2-(2,2,2-trifluoroethoxy)phenyl]-piperazine. The crude was purified by flash chromatography, eluting with ethyl acetate/2N ammonia solution in methanol 95:5, followed by crystallisation from ethyl acetate to give the title compound (16%). M.p.191–194° C.

| ¹H-NMR (200 MHz, CDCl₃, δ) | | | |
|---|---|---|---|
| 8.53 | bt | 1H | CONH |
| 8.22–8.40 | m | 2H | H7 and H5 |
| 8.05 | bs | 1H | CONHH |
| 7.45 | dd | 1H | H6 |
| 6.62–6.85 | m | 3H | phenyl CHs |
| 5.95 | bs | 1H | CONHH |
| 4.35 | q | 2H | OCH₂CF₃ |
| 3.42–3.80 | m | 8H | 6 piperazine Hs and NHCH₂CH₂CH₂N |
| 3.12–3.40 | m | 2H | NHCH₂CH₂CH₂N |
| 2.90–3.12 | m | 2H | 2 piperazine Hs |
| 2.42 | s | 3H | CH₃C |
| 2.20–2.38 | m | 2H | NHCH₂CH₂CH₂N |

EXAMPLE 9

2-Carbamoyl-8-<3-{4-[2-methoxy-5-(2,2,2-trifluoroethoxy)phenyl]-1-piperazinyl}-propylcarbamoyl>-3-methyl-4-oxo-4H-1-benzopyran a) 1-t-Butoxycarbonyl-4-(5-hydroxy-2-methoxyphenyl)piperazine (Compound 9A)

A solution of 8 g of 1-(5-hydroxy-2-methoxyphenyl)piperazine dihydrobromide (prepared as described in U.S. Pat. No. 5,605,896, Leonardi A. et al.) and 3.17 g of anhydrous potassium carbonate in 30 mL of water was evaporated to dryness in vacuo. 100 mL of anhydrous tetrahydrofuran and 5.18 g of di-t-butyl dicarbonate (BOC₂O) were added to the residue and the mixture was stirred at room temperature for 2 hours, followed by addition of 100 mL of anhydrous tetrahydrofuran. The suspension was filtered and the solvent was removed in vacuo. The residue was dissolved in 200 mL of chloroform and the solution was washed with 3×50 mL of 5% sodium hydrogen carbonate and 2×50 mL of water, and dried over sodium sulphate. The solvent was removed at reduced pressure and the residue was purified by flash chromatography (petroleum ether/ethyl acetate 75:25) to give 1.91 g (28.7%) of Compound 9A and 1.58 g (35.7%) of 1-t-butoxycarbonyl-4-(5-t-butoxycarbonyloxy-2-methoxyphenyl)piperazine. A solution of this by-product, 40 mL of methanol and 6 mL of 1N sodium hydroxide was maintained overnight at room temperature. The mixture was neutralised with acetic acid; the solvent was removed at reduced pressure and the residue dissolved in 40 mL of chloroform. After washing with 3×10 mL of water, the organic layer was dried over sodium sulphate and the solvent evaporated in vacuo to recover an additional 1.15 g (17.2%) of Compound 9A (total yield 45.9%).

| ¹H-NMR (200 MHz, CDCl₃, δ) | | | |
|---|---|---|---|
| 6.70 | d | 1H | phenyl H3 |
| 6.45–6.53 | m | 2H | phenyl H4 and H6 |
| 5.77 | bs | 1H | OH |
| 3.78 | s | 3H | CH₃O |
| 3.48–3.68 | m | 4H | 2 piperazine CH₂s |
| 2.82–3.05 | m | 4H | 2 piperazine CH₂s |
| 1.48 | s | 9H | (CH₃)₃C | b) 1-t-Butoxycarbonyl-4-[2-methoxy-5-(2,2,2-trifluoroethoxy)phenyl]piperazine (Compound 9B)

A stirred mixture of 2.83g of Compound 9A, 6.05 g of cesium carbonate and 2.95 g of 2,2,2-trifluoroethyl p-toluenesulphonate in 60 mL of acetonitrile was refluxed for 16 hours. The solvent was evaporated at reduced pressure; 90 mL of brine was added to the residue and the mixture was extracted with 3×40 mL of ethyl acetate. The organic layer was washed with 3×20 mL of water and 20 mL of brine, and dried over sodium sulphate. The solvent was removed at reduced pressure and the residue purified by flash chromatography (petroleum ether/ethyl acetate gradient 95:5 to 80:20). The solvents were removed in vacuo to give 1.86 g (52%) of Compound 9B as a white solid. M.p. (98) 102–105° C.

| ¹H-NMR (200 MHz, CDCl₃, δ) | | | |
|---|---|---|---|
| 6.77 | d | 1H | phenyl H3 |
| 6.45–6.63 | m | 2H | phenyl H4 and H6 |
| 4.28 | q | 2H | CF₃CH₂O |
| 3.84 | s | 3H | CH₃O |
| 3.53–3.68 | m | 4H | 2 piperazine CH₂s |
| 2.90–3.06 | m | 4H | 2 piperazine CH₂s |
| 1.48 | s | 9H | (CH₃)₃C | c) 1-[2-Methoxy-5-(2,2,2-trifluoroethoxy)phenyl]piperazine.1.9 HCl (Compound 9C)

A solution of 2.42 mL of trifluoroacetic acid in 30 mL of anhydrous dichloromethane was added dropwise at 3–5° C. to a stirred solution of 1.17 g of Compound 9B in 40 mL of anhydrous dichloromethane. The mixture was maintained overnight at room temperature, washed with 2×30 mL of 2N sodium hydroxide and extracted with 3×15 mL of 2N hydrochloric acid. The aqueous acid layer was washed with 2×20 mL of diethyl ether, alkalinised with 35% sodium hydroxide at 5–10° C. and extracted with 3×30 mL of diethyl ether. The organic layer was dried over sodium sulphate and the solvent was removed in vacuo to give 0.78 g (89%) of Compound 9C base as a thick oil. A solution of this base in diethyl ether was treated with coal, filtered and acidified with 3.6N anhydrous hydrogen chloride in diethyl ether to give the hydrochloride salt, recovered by filtration and crystallised from acetonitrile and ethanol (15:2). M.p. (188) 202–208° C. (dec.).

| $^1$H-NMR (200 MHz, DMSO-d$_6$, δ) | | | |
|---|---|---|---|
| 9.18 | bs | 2.9H | NH$^+$ |
| 6.90 | d | 1H | phenyl H3 |
| 6.67 | dd | 1H | phenyl H4 |
| 6.59 | d | 1H | phenyl H6 |
| 4.66 | q | 2H | CF$_3$CH$_2$O |
| 3.74 | s | 3H | CH$_3$O |
| 3.18 | bs | 8H | Piperazine CH$_2$s | d) 2-Carbamoyl-8-<3-{4-[2-methoxy-5-(2,2,2-trifluoroethoxy)phenyl]-1-piperazinyl}propylcarbamoyl>-3-methyl-4-oxo-4H-1-benzopyran This compound was prepared as described in Ex. 7b), but substituting Compound 9C for 1-[4-fluoro-2-(2,2,2-trifluoroethoxy)phenyl]piperazine. The crude was purified by flash chromatography, eluting with ethyl acetate/2N ammonia solution in methanol 92:8, followed by crystallisation from ethyl acetate to give the title compound (37%). M.p. 181–183° C.

| $^1$H-NMR (200 MHz, CDCl$_3$, δ) | | | |
|---|---|---|---|
| 8.65 | bt | 1H | CONH |
| 8.28 | dd | 1H | H5 (H7) |
| 7.92 | dd | 1H | H7 (H5) |
| 7.68 | bs | 1H | CONHH |
| 7.39 | dd | 1H | H6 |
| 6.73 | d | 1H | phenyl H3 (H4) |
| 6.38–6.52 | m | 2H | phenyl H4 (H3) and H6 |
| 5.80 | bs | 1H | CONHH |
| 4.30 | q | 2H | OCH$_2$CF$_3$ |
| 3.80 | s | 3H | CH$_3$O |
| 3.62 | dt | 2H | NHCH$_2$CH$_2$CH$_2$N |
| 2.85–3.12 | m | 4H | 2 piperazine CH$_2$s |
| 2.55–2.80 | m | 6H | 2 piperazine CH$_2$s and NHCH$_2$CH$_2$CH$_2$N |
| 2.50 | s | 3H | CH$_3$C |
| 1.80–1.98 | m | 2H | NHCH$_2$CH$_2$CH$_2$N |

EXAMPLE 10

2-Carbamoyl-8-<3-{4-[2-(2,2,2-trifluoroethoxy)phenyl]-1-piperazinyl}-propylcarbamoyl>-3-methyl-4-oxo-4H-1-benzopyran This compound was prepared as described in Ex. 7b), but substituting 1-[2-(2,2,2-trifluoroethoxy)phenyl]piperazine (prepared as described in European Patent EP 0748800, Bantle et al.) for 1-[4-fluoro-2-(2,2,2-trifluoroethoxy)phenyl]piperazine. The crude obtained from flash chromatography was washed with boiling ethyl acetate, instead of being crystallised, to afford the title compound (39%). M.p. 201–203° C.

| $^1$H-NMR (200 MHz, CDCl$_3$, δ) | | | |
|---|---|---|---|
| 8.75 | bt | 1H | CONH |
| 8.30 | dd | 1H | H5 (H7) |
| 7.95 | dd | 1H | H7 (H5) |
| 7.75 | bs | 1H | CONHH |
| 7.40 | dd | 1H | H6 |
| 6.80–7.12 | m | 4H | phenyl ring aromatics |
| 5.80 | bs | 1H | CONHH |
| 4.35 | q | 2H | OCH$_2$CF$_3$ |

-continued

| $^1$H-NMR (200 MHz, CDCl$_3$, δ) | | | |
|---|---|---|---|
| 3.62 | dt | 2H | NHCH$_2$CH$_2$CH$_2$N |
| 2.85–3.10 | m | 4H | 2 piperazine CH$_2$s |
| 2.55–2.80 | m | 6H | 2 piperazine CH$_2$s and NHCH$_2$CH$_2$CH$_2$N |
| 2.50 | s | 3H | CH$_3$ |
| 1.80–2.03 | m | 2H | NHCH$_2$CH$_2$CH$_2$N |

EXAMPLE 11

8-{3-[4-(5-Chloro-2-methoxyphenyl)-1-piperazinyl]propylcarbamoyl}-2-cyano-3-methyl-4-oxo-4H-1-benzopyran Method A 2.62 g of triphenylphosphine and 10 mL of carbon tetrachloride were added to a suspension of 0.52 g of the Compound of Ex. 1 in 30 mL of 1,2-dichloroethane. The resulting mixture was stirred at reflux for 8 hours and cooled to room temperature. The solvents were evaporated off in vacuo. The crude was purified by flash chromatography eluting with ethyl acetate/2N ammonia solution in methanol gradient from 98:2 to 94:6, followed by crystallisation from ethyl acetate to give 0.070 g (14%) of the title compound.

Method B

A mixture of 1.11 mL of phosphorus oxychloride and 50 mL of dimethylformamide was stirred at 0° C. for 15 minutes and then at room temperature for 30 minutes. 1.23 g of the Compound of Ex. 1 was then added and the reaction mixture was stirred at room temperature for 2 hours, poured into water, neutralised with an aqueous solution of potassium carbonate and filtered to afford the title compound, which was crystallised from ethyl acetate to give 0.86 g (60%). M.p. 183–185° C.

| $^1$H-NMR (200 MHz, CDCl$_3$, δ) | | | |
|---|---|---|---|
| 8.18–8.38 | m | 2H | H5 and H7 |
| 7.70–7.86 | br | 1H | NH |
| 7.53 | dd | 1H | H6 |
| 6.91 | dd | 1H | phenyl H4 |
| 6.73 | d | 1H | phenyl H3 |
| 6.67 | d | 1H | phenyl H6 |
| 3.82 | s | 3H | CH$_3$O |
| 3.68 | dt | 2H | NHCH$_2$CH$_2$CH$_2$ |
| 2.85–3.04 | m | 4H | 2 piperazine CH$_2$s |
| 2.55–2.78 | m | 6H | 2 piperazine CH$_2$s and NHCH$_2$CH$_2$CH$_2$N |
| 2.32 | s | 3H | CH$_3$C |
| 1.89 | tt | 2H | NHCH$_2$CH$_2$CH$_2$N |

EXAMPLE 12

2-Carbamoyl-8-{3-[4-(5-chloro-2-hydroxyphenyl)-1-piperazinyl]-propylcarbamoyl}-3-methyl-4-oxo-4H-1-benzopyran a) 1-(5-Chloro-2-hydroxyphenyl)piperazine dihydrobromide (Compound 12A)

A suspension of 5.5 g of 1-(5-chloro-2-methoxyphenyl)piperazine in 40 mL of 62% hydrobromic acid was stirred at reflux for 30 hours. After cooling to room temperature the mixture was filtered by suction and the solid was washed on the funnel with acetone affording 6.02 g of the title compound. M.p.>270° C. (ethanol).

| ¹H-NMR (200 MHz, DMSO-d₆, δ) | | | |
|---|---|---|---|
| 9.35–9.80 | br | 2H | NH₂⁻ |
| 8.60–9.05 | br | 2H | NH⁻, OH |
| 6.70–6.97 | m | 3H | phenyl CHs |
| 3.00–3.38 | m | 8H | piperazine CH₂s | b) 2-Carbamoyl-8-{3-[4-(5-Chloro-2-hydroxyphenyl)-1-piperazinyl]-propylcarbamoyl}-3-methyl-4-oxo-4H-1-benzopyran This compound was prepared as described in Ex. 7b), substituting Compound 12A for 1-[4-fluoro-2-(2,2,2-trifluoroethoxy)phenyl]piperazine. Extraction with chloroform followed by purification by flash chromatography (chloroform/2N ammonia solution in methanol 95:5) and crystallisation from ethyl acetate afforded the title compound (9%). M.p. 116–158° C.

| ¹H-NMR (200 MHz, CDCl₃, δ) | | | |
|---|---|---|---|
| 8.30–8.45 | m | 2H | H5 (H7) and CONH |
| 7.95 | d | 1H | H7 (H5) |
| 7.66 | bs | 1H | CONH<u>H</u> |
| 7.51 | dd | 1H | H6 |
| 7.05 | dd | 1H | phenol H4 |
| 6.80–6.95 | m | 2H | phenol H3 and H6 |
| 5.83 | bs | 1H | CON<u>H</u>H |
| 3.50–3.80 | m | 2H | NHC<u>H</u>₂CH₂CH₂N |
| 2.54–2.98 | m | 11H | piperazine CH₂s, OH and NHCH₂CH₂C<u>H</u>₂N |
| 2.49 | m | 3H | CH₃C |
| 1.75–1.98 | m | 2H | NHCH₂C<u>H</u>₂CH₂N |

EXAMPLE 13

2-Carbamoyl-8-{3-[4-(5-chloro-2-trifluoromethanesulphonyloxyphenyl)-1-piperazinyl]propylcarbamoyl}-3-methyl-4-oxo-4H-1-benzopyran 0.49 g of N-phenyltrifluoromethanesulphonimide and 0.21 mL of triethylamine were added to a solution of 0.3 g of the compound of Ex. 12 in 10 mL of 1,2-dichloroethane. The resulting solution was stirred at 60° C. for 6 hours. An additional 0.33 g of N-phenyltrifluoromethanesulphonimide and 0.21 mL of triethylamine were added, the solution was stirred at 60° C. for 6 hours and cooled to room temperature. The organic phase was washed with water and dried over sodium sulphate, and the solvent was evaporated off. The crude was purified by flash chromatography (ethyl acetate/2N ammonia solution in methanol 95:5), and by crystallisation from ethyl acetate to give 0.09 g (24%) of the title compound. M.p. 150–156° C.

| ¹H-NMR (200 MHz, CDCl₃, δ) | | | |
|---|---|---|---|
| 8.28–8.40 | m | 2H | H5 (H7) and CONH |
| 8.04 | d | 1H | H7 (H5) |
| 7.66 | bs | 1H | CONH<u>H</u> |
| 7.48 | dd | 1H | H6 |
| 7.05 | dd | 2H | phenyl Hs |
| 7.00 | d | 1H | phenyl H |
| 5.8 | bs | 1H | CON<u>H</u>H |
| 3.65 | dt | 2H | NHC<u>H</u>₂CH₂CH₂N |
| 2.82–3.20 | m | 10H | piperazine CH₂s and NHCH₂CH₂C<u>H</u>₂N |
| 2.49 | m | 3H | CH₃C |
| 1.92–2.15 | m | 2H | NHCH₂C<u>H</u>₂CH₂N |

EXAMPLE 14

8-{3-[4-(2-Trifluoromethanesulphonyloxyphenyl)-1-piperazinyl]-propylcarbamoyl}-3-methyl-4-oxo-2-phenyl-4H-1-benzopyran hydrochloride.0.5 H₂O 1.41 g of N-phenyltrifluoromethanesulphonimide was added at room temperature to a stirred solution of 1.22 g of 8-{3-[4-(2-hydroxyphenyl)-1-piperazinyl]-propylcarbamoyl}-3-methyl-4-oxo-2-phenyl-4H-1-benzopyran (prepared as described in U.S. Pat. No. 5,474,994, Leonardi et al.) and 0.84 mL of triethylamine in 60 mL of anhydrous dichloromethane. The mixture was kept for 24 hours at 22–25° C. 1.68 mL of triethylamine and 2.73 g of N-phenyltrifluoromethanesulphonimide were added over the next 5 days. The resulting turbid reaction mixture was washed with 3×50 mL of 20% sodium carbonate and 6×50 mL of water, then dried over sodium sulphate. The solvent was removed at reduced pressure to give a residue which was purified by flash chromatography (chloroform/3N methanolic ammonia 100:1). The solvents were removed in vacuo, the residue was dissolved in dichloromethane and the solution was acidified with 3N anhydrous hydrogen chloride in diethyl ether. The solvent was evaporated off in vacuo and the residue was crystallised from acetonitrile to afford 0.66 g (40%) of the title compound. M.p. 203–204° C.

| ¹H-NMR (200 MHz, DMSO-d₆, δ) | | | |
|---|---|---|---|
| 10.72–11.07 | br | 1H | NH⁺ |
| 8.62–8.82 | m | 1H | CONH |
| 8.20 | dd | 1H | H5 (H7) |
| 7.95 | dd | 1H | H7 (H5) |
| 7.72–7.90 | m | 2H | 2-phenyl ring H2 and H6 |
| 7.15–7.72 | m | 8H | H6; 2-phenyl H3, H4 and H5; CHs of CF₃SO₃Ph ring |
| 3.05–3.58 | m | 11H | Piperazine CH₂s, CONHC<u>H</u>₂CH₂CH₂, H₂O |
| 2.75–3.05 | m | 2H | CONHCH₂CH₂C<u>H</u>₂ |
| 2.09 | s | 3H | CH₃ |
| 1.80–2.05 | m | 2H | CONHCH₂C<u>H</u>₂CH₂ |

EXAMPLE 15

8-<3-{4-[2-(2,2,2-Trifluoroethoxy)phenyl]-1-piperazinyl}propylcarbamoyl>-3-methyl-4-oxo-2-phenyl-4H-1-benzopyran A mixture of 0.89 g of 8-(3-chloropropylcarbamoyl)-3-methyl-4-oxo-2-phenyl-4H-1-benzopyran (prepared as described in U.S. Pat. No. 5,474,994, Leonardi et al.), 0.65 g of 1-[2-(2,2,2-trifluoroethoxy)phenyl]piperazine (prepared as described in European Patent EP 748800, Bantle G. W. et al.) and 0.35 g of anhydrous potassium carbonate was heated at 185– 195° C. for 30 minutes. After cooling to 25° C., 50 mL of chloroform was added and the mixture was kept overnight at room temperature. The suspension was washed with 3×30 mL of water, 3×30 mL of 10% sodium carbonate and 3×30 mL of water and the resulting solution was dried over sodium sulphate. The solvent was removed at reduced pressure and the residue was purified by flash chromatography (chloroform/3N methanolic ammonia 100:1). The residue was crystallised from acetonitrile to afford 0.56 g (39%) of the title compound. M.p. 146–148° C.

| $^1$H-NMR (200 MHz, DMSO-d$_6$, δ) | | | |
|---|---|---|---|
| 8.45–8.60 | m | 1H | CONH |
| 8.12 | dd | 1H | H5 (H7) |
| 7.90 | dd | 1H | H7 (H5) |
| 7.71–7.85 | m | 2H | H2 and H6 of 2-phenyl ring |
| 7.43–7.65 | m | 4H | H3, H4 and H5 of 2-phenyl ring and H6 |
| 6.85–7.08 | m | 4H | CHs of trifluoroethoxyphenyl ring |
| 4.69 | q | 2H | OCH$_2$CF$_3$ |
| 3.20–3.40 | m | 2H | CONHC$\underline{H}_2$CH$_2$CH$_2$ |
| 2.80–3.05 | m | 4H | 2 piperazine CH$_2$s |
| 2.22–2.48 | m | 6H | 2 piperazine CH$_2$s, CONHCH$_2$CH$_2$C$\underline{H}_2$ |
| 2.08 | s | 3H | CH$_3$ |
| 1.55–1.80 | m | 2H | CONHCH$_2$C$\underline{H}_2$CH$_2$ |

EXAMPLE 16

8-{3-[4-(2-Trifluoromethoxyphenyl)-1-piperazinyl]propylcarbamoyl}-3-methyl-4-oxo-2-phenyl-4H-1-benzopyran The title compound was prepared following the procedure described in Ex. 15, but using 1-(2-trifluoromethoxyphenyl)piperazine (prepared as described in European Patent EP 748800, Bantle G. W. et al.) in place of 1-[2-(2,2,2-trifluoroethoxy)phenyl]piperazine. The flash chromatography was carried out with ethyl acetate/methanol (gradient from 100:0 to 100:5). Yield 34%. M.p. 103–112° C.

| $^1$H-NMR (200 MHz, CDCl$_3$, δ) | | | |
|---|---|---|---|
| 8.30–8.45 | m | 2H | H5, H7 |
| 7.63–7.80 | m | 3H | CONH, H2 and H6 of 2-phenyl ring |
| 7.53–7.63 | m | 3H | H3, H4, H5 of 2-phenyl ring |
| 7.48 | t | 1H | H6 |
| 7.10–7.30 | m | 2H | Trifluoromethoxyphenyl H4 and H5 |
| 6.80–7.05 | m | 2H | Trifluoromethoxyphenyl H3 and H6 |
| 3.48–3.65 | m | 2H | CONHC$\underline{H}_2$CH$_2$CH$_2$ |
| 2.82–2.97 | m | 4H | 2 piperazine CH$_2$s |
| 2.30–2.50 | m | 6H | 2 piperazine CH$_2$s, CONHCH$_2$CH$_2$C$\underline{H}_2$ |
| 2.20 | s | 3H | CH$_3$ |
| 1.60–1.82 | m | 2H | CONHCH$_2$C$\underline{H}_2$CH$_2$ |

EXAMPLE 17

8-{3-[4-(2-Methoxy-5-trifluoromethylphenyl)-1-piperazinyl]propylcarbamoyl}-3-methyl-4-oxo-2-phenyl-4H-1-benzopyran a) 1-(2-Methoxy-5-trifluoromethylphenyl)piperazine (Compound 17A)

A mixture of 6.65 g of 2-methoxy-5-trifluoromethylaniline, 6.21 g of bis-(2-chloroethyl)amine hydrochloride, 4.71 g of anhydrous potassium carbonate and 0.34 g of anhydrous potassium iodide in 70 mL of n-butanol was refluxed for 50 hours. The solvent was removed at reduced pressure and the residue was taken up in 400 mL of diethyl ether. The suspension was acidified with 3N anhydrous hydrogen chloride in diethyl ether and stirred at room temperature for 3 hours. The solid was collected by filtration and dissolved in 50 mL of water. The solution was acidified with 36% hydrochloric acid, washed with 3×50 mL of diethyl ether, alkalinised with excess 36% sodium hydroxide and extracted with 2×70 mL of diethyl ether. The organic layer was dried over sodium sulphate and evaporated to dryness at reduced pressure to give a residue which was purified twice by flash chromatography, first using chloroform/3N methanolic ammonia 100:3 and subsequently using the upper layer of a 4:5:1 mixture of water, n-butanol and glacial acetic acid. The solvents were removed by evaporation in vacuo to give a residue which was dissolved in water. The mixture was alkalinised with 2N sodium hydroxide and extracted with chloroform; the organic layer was dried over sodium sulphate and the solvent was removed under reduced pressure to afford 1.42 g (16%) of Compound 17A as an oil.

| $^1$H-NMR (200 MHz, CDCl$_3$, δ) | | | |
|---|---|---|---|
| 7.20–7.35 | m | 1H | methoxyphenyl H4 |
| 7.11 | d | 1H | methoxyphenyl H6 |
| 6.89 | d | 1H | methoxyphenyl H3 |
| 3.91 | s | 3H | CH$_3$O |
| 3.00–3.10 | s | 8H | piperazine CH$_2$s |
| 1.81 | bs | 1H | NH | b) 8-{3-[4-(2-Methoxy-5-trifluoromethylphenyl)-1-piperazinyl]propylcarbamoyl}-3-methyl-4-oxo-2-phenyl-4H-1-benzopyran The title compound was prepared following the procedure described in Ex. 15, but substituting Compound 17A for 1-[2-(2,2,2-trifluoroethoxy)phenyl]piperazine. Crystallisation was from 95% ethanol instead of acetonitrile. Yield 45%. M.p. 173–176° C.

| $^1$H-NMR (200 MHz, DMSO-d$_6$, δ) | | | |
|---|---|---|---|
| 8.45–8.60 | m | 1H | CONH |
| 8.18 | dd | 1H | H5 (H7) |
| 7.90 | dd | 1H | H7 (H5) |
| 7.70–7.85 | m | 2H | H2 and H6 of 2-phenyl ring |
| 7.45–7.65 | m | 4H | H6; H3, H4 and H5 of 2-phenyl ring |
| 7.31 | dd | 1H | methoxyphenyl H4 |
| 6.98–7.16 | m | 2H | methoxyphenyl H6 and H3 |
| 3.86 | s | 3H | OCH$_3$ |
| 3.18–3.40 | m | 2H | CONHC$\underline{H}_2$CH$_2$CH$_2$ |
| 2.32–3.07 | m | 4H | 2 piperazine CH$_2$s |
| 2.20–2.45 | m | 6H | 2 piperazine CH$_2$s, CONHCH$_2$CH$_2$C$\underline{H}_2$ |
| 2.08 | s | 3H | CH$_3$ |
| 1.51–1.79 | m | 2H | CONHCH$_2$C$\underline{H}_2$CH$_2$ |

EXAMPLE 18

8-{3-[4-(5-Cyano-2-methoxyphenyl)-1-piperazinyl]propylcarbamoyl}-3-methyl-4-oxo-2-phenyl-4H-1-benzopyran a) 5-Cyano-2-methoxynitrobenzene (Compound 18A)

A suspension of 8.37 g of 4-hydroxy-3-nitrobenzonitrile, 27.64 g of anhydrous potassium carbonate and 6 mL of dimethyl sulphate in 60 mL of acetonitrile was stirred at reflux for 2 hours. The solvent was removed by evaporation in vacuo. The residue was taken up in 100 mL of water and extracted with 3×80 mL of chloroform. The combined organic layers were dried over sodium sulphate and the solvent was evaporated off to afford 8.8 g (98.8%) of Compound 18A as an ivory solid.

| ¹H-NMR (200 MHz, DMSO-d₆, δ) | | | |
|---|---|---|---|
| 8.46 | d | 1H | H6 |
| 8.13 | dd | 1H | H4 |
| 7.54 | d | 1H | H3 |
| 4.00 | s | 3H | CH₃O | b) 5-Cyano-2-methoxyaniline (Compound 18B)

A mixture of 8.8 g of Compound 18A and 46.8 g of stannous chloride dihydrate in 250 mL of 95% ethanol was refluxed for 1 hour. The solvent was evaporated off in vacuo and the residue was taken up with 200 mL of water. The mixture was acidified with 37% HCl, then alkalinised with 35% sodium hydroxide and extracted with 3×200 mL of diethyl ether. The combined organic layers were washed with 50 mL of water, dried over sodium sulphate and evaporated to dryness in vacuo to afford 6.90 g (94.2%) of Compound 18B as an ivory solid.

| ¹H-NMR (200 MHz, DMSO-d₆, δ) | | | |
|---|---|---|---|
| 6.82–7.05 | m | 3H | H3, H4 and H6 |
| 5.20 | bs | 2H | NH₂ |
| 3.82 | s | 3H | CH₃O | c) 1-(5-Cyano-2-methoxyphenyl)piperazine. 0.25 H₂O (Compound 18C)

A mixture of 6.38 g of Compound 18B, 7.1 g of potassium iodide, 5.95 g of anhydrous potassium carbonate and 7.68 g of 98% bis-(2-chloroethyl)amine hydrochloride in 150 mL of n-butanol was refluxed for 43 hours under nitrogen. After this time, an additional 3.4 g of 98% bis-(2-chloroethyl) amine hydrochloride and 3 g (21 mmol) of anhydrous potassium carbonate were added and reflux was continued for a further 14 hours. The solvent was removed under reduced pressure. The residue was taken up in 100 mL of water, acidified with 37% hydrochloric acid, then alkalinised with 35% sodium hydroxide and extracted with 3×100 mL of ethyl acetate. The organic layer was washed with 20 mL of brine, dried over sodium sulphate and evaporated to dryness in vacuo. The residue was purified twice by flash chromatography (chloroform/2.7N methanolic ammonia gradient from 100:1 to 100:5; then chloroform: 2.7N methanolic ammonia gradient from 100:5 to 80:20) to afford 2.76 g (29%) of the title compound as an ivory solid. M.p. (78) 100–106° C.

| ¹H-NMR (200 MHz, CDCl₃, δ) | | | |
|---|---|---|---|
| 7.33 | dd | 1H | H4 |
| 7.13 | d | 1H | H6 |
| 6.87 | d | 1H | H3 |
| 3.92 | s | 3H | CH₃O |
| 2.95–3.15 | m | 8H | piperazine CH₂s |
| 1.97 | bs | 1.5H | NH, 0.25 H₂O | d) 8-{3 -[4-(5-Cyano-2-methoxyphenyl)-1-piperazinyl] propylcarbamoyl}-3-methyl-4-oxo-phenyl-4H-1-benzopyran The title compound was prepared following the procedure described in Ex. 15, but using Compound 18C in place of 1-[2-(2,2,2-trifluoroethoxy)phenyl]piperazine. The flash chromatography was carried out with chloroform/2.7 N methanolic ammonia, gradient from 100:1 to 100:2 Yield 53% M.p. 188–193° C.

| ¹H-NMR (200 MHz, CDCl₃, δ) | | | |
|---|---|---|---|
| 8.40 | dd | 2H | H5 and H7 |
| 7.63–7.80 | m | 2H | H2 and H6 of 2-phenyl ring |
| 7.53–7.62 | m | 4H | H3, H4 and H5 of 2-phenyl ring, CONH |
| 7.50 | t | 1H | H6 |
| 7.32 | dd | 1H | methoxyphenyl H4 |
| 7.05 | d | 1H | methoxyphenyl H6 |
| 6.86 | d | 1H | methoxyphenyl H3 |
| 3.90 | s | 3H | CH₃O |
| 3.50–3.65 | m | 2H | CONHC<u>H</u>₂CH₂CH₂ |
| 2.85–3.05 | m | 4H | 2 piperazine CH₂s |
| 2.30–2.58 | m | 6H | 2 piperazine CH₂s, CONHCH₂CH₂C<u>H</u>₂ |
| 2.21 | s | 3H | CH₃ |
| 1.60–1.83 | m | 2H | CONHCH₂C<u>H</u>₂CH₂ |

EXAMPLE 19

8-<3-{4-[4-Fluoro-2-(2,2,2-trifluoroethoxy)phenyl]-1-piperazinyl}propylcarbamoyl>-3-methyl-4-oxo-2-phenyl-4H-1-benzopyran The title compound was prepared following the procedure described in Ex. 15, but using 1-[4-fluoro-2-(2,2,2-trifluoroethoxy)phenyl]piperazine (prepared as described in European Patent EP 748800, Bantle et al.) in place of 1-[2-(2,2,2-trifluoroethoxy)phenyl]-piperazine. The flash chromatography was carried out with ethyl acetate/methanol 100:3. Yield 73.4%, as an ivory solid.

| ¹H-NMR (200 MHz, CDCl₃, δ) | | | |
|---|---|---|---|
| 8.30–8.45 | m | 2H | H5 and H7 |
| 7.61–7.90 | m | 3H | CONH, H2 and H6 of 2-phenyl ring |
| 7.50–7.61 | m | 3H | H3, H4 and H5 of 2-phenyl ring |
| 7.45 | t | 1H | H6 |
| 6.82 | dd | 2H | fluorophenyl H5 and H6 |
| 6.60 | dd | 1H | fluorophenyl H3 |
| 4.35 | q | 2H | CH₂CF₃ |
| 3.46–3.65 | m | 2H | CONHC<u>H</u>₂CH₂CH₂ |
| 2.73–2.94 | m | 4H | 2 piperazine CH₂s |
| 2.30–2.55 | m | 6H | CONHCH₂CH₂C<u>H</u>₂, 2 piperazine CH₂s |
| 2.20 | s | 3H | CH₃ |
| 1.60–1.80 | m | 2H | CONHCH₂C<u>H</u>₂CH₂ |

EXAMPLE 20

8-<3-{4-[5-Fluoro-2-(2,2,2-trifluoroethoxy)phenyl]-1-piperazinyl}-propylcarbamoyl>-3-methyl-4-oxo-2-phenyl-4H-1-benzopyran The title compound was prepared following the procedure described in Ex. 15, but using Compound 8C instead of 1-[2-(2,2,2-trifluoroethoxy)phenyl]piperazine. The flash chromatography was carried out with chloroform/2N-methanolic-ammonia, gradient from 100:1 to 100:3. Yield 66.5%, as an ivory solid. M.p. 162–166° C.

| ¹H-NMR (200 MHz, CDCl₃, δ) | | | |
|---|---|---|---|
| 8.38 | d | 2H | H5 and H7 |
| 7.75–7.80 | m | 2H | H2 and H6 of 2-phenyl ring |
| 7.55–7.75 | m | 4H | H3, H4 and H5 of 2-phenyl ring, CONH |
| 7.50 | t | 1H | H6 |

-continued

| $^1$H-NMR (200 MHz, CDCl$_3$, δ) | | | |
|---|---|---|---|
| 6.86 | dd | 1H | trifluoroethoxyphenyl H3 |
| 6.50–6.70 | m | 2H | trifluoroethoxyphenyl H4 and H6 |
| 4.31 | q | 2H | OCH$_2$CF$_3$ |
| 3.50–3.65 | m | 2H | CONHCH$_2$CH$_2$CH$_2$ |
| 2.85–3.05 | m | 4H | 2 piperazine CH$_2$s |
| 2.30–2.55 | m | 6H | 2 piperazine CH$_2$s, CONHCH$_2$CH$_2$CH$_2$ |
| 2.20 | s | 3H | CH$_3$ |
| 1.60–1.85 | m | 2H | CONHCH$_2$CH$_2$CH$_2$ |

EXAMPLE 21

8-<3-{4-[2-Methoxy-5-(2,2,2-trifluoroethoxy)phenyl]-1-piperazinyl}-propylcarbamoyl>-3-methyl-4-oxo-2-phenyl-4H-1-benzopyran The title compound was prepared following the procedure described in Ex. 15, but substituting Compound 9C for 1-[2-(2,2,2-trifluoroethoxy)phenyl]piperazine. The crystallisation was from ethanol rather than acetonitrile. Yield 27.7%, as a white solid. M.p. (93) 138–143° C.

| $^1$H-NMR (200 MHz, DMSO-d$_6$, δ) | | | |
|---|---|---|---|
| 8.80–8.95 | m | 2H | H5 and H7 |
| 7.65–7.70 | m | 3H | H2 and H6 of 2-phenyl ring, CONH |
| 7.52–7.65 | m | 3H | H3, H4 and H5 of 2-phenyl ring |
| 7.45 | dd | 1H | H6 |
| 6.74 | dd | 1H | methoxyphenyl H3 |
| 6.42–6.56 | m | 2H | methoxyphenyl H4 and H6 |
| 4.30 | q | 2H | CF$_3$CH$_2$O |
| 3.80 | s | 3H | CH$_3$O |
| 3.48–3.65 | m | 2H | CONHCH$_2$CH$_2$CH$_2$ |
| 2.80–3.05 | m | 4H | 2 piperazine CH$_2$s |
| 2.30–2.65 | m | 6H | 2 piperazine CH$_2$s, CONHCH$_2$CH$_2$CH$_2$ |
| 2.21 | s | 3H | CH$_3$ |
| 1.60–1.85 | m | 2H | CONHCH$_2$CH$_2$CH$_2$ |

EXAMPLE 22

8-<3-{4-[5-Chloro-2-(2,2,2-trifluoroethoxy)phenyl]-1-piperazinyl}-propylcarbamoyl>-3-methyl-4-oxo-2-phenyl-4H-1-benzopyran a) 1-t-Butoxycarbonyl-4-(5-chloro-2-hydroxyphenyl)piperazine (Compound 22A)

The title compound was synthesised following the procedure described in Ex. 9a, but using Compound 12A in place of 1-(5-hydroxy-2-methoxyphenyl)piperazine. Workup was by flash chromatography (petroleum ether/ethyl acetate 90:10) affording Compound 22A (92.3%) as a white solid, used in the next step without further purification.

| $^1$H-NMR (200 MHz, CDCl$_3$, δ) | | | |
|---|---|---|---|
| 7.00–7.12 | m | 2H | H4 and H6 of phenyl ring |
| 6.90 | dd | 1H | H3 of phenyl ring |
| 6.73 | bs | 1H | OH |
| 3.51–3.65 | m | 4H | 2 piperazine CH$_2$s |
| 2.71–2.87 | m | 4H | 2 piperazine CH$_2$s |
| 1.49 | s | 9H | (CH$_3$)$_3$C | b) 1-t-Butoxycarbonyl-4-[5-chloro-2-(2,2,2-trifluoroethoxy)phenyl]piperazine (Compound 22B)

The title compound was prepared following the method described in Ex. 9b, but substituting Compound 22A for Compound 9A. The crude oily residue was purified by flash chromatography eluting sequentially with dichloromethane, petroleum ether and petroleum ether/ethyl acetate 90:10. The solvents of the pure collected fractions were removed at reduced pressure to give Compound 22B (68.5%) as a thick oil, used in the next step without further purification.

| $^1$H-NMR (200 MHz, CDCl$_3$, δ) | | | |
|---|---|---|---|
| 6.75–7.00 | m | 3H | Phenyl CHs |
| 4.36 | q | 2H | CF$_3$CH$_2$O |
| 3.49–3.65 | m | 4H | 2 piperazine CH$_2$s |
| 2.92–3.08 | m | 4H | 2 piperazine CH$_2$s |
| 1.48 | s | 9H | (CH$_3$)$_3$C | c) 1-[5-Chloro-2-(2,2,2-trifluoroethoxy)phenyl]piperazine hydrochloride (Compound 22C)

The title compound was synthesised following the procedure described in Ex. 9c, but using Compound 22B instead of Compound 9B. After the work-up procedure the solvents were removed by evaporation in vacuo to afford 85.1% of Compound 22C as a solid ivory base, used in the next step without further purification. A solution of the base in diethyl ether was treated with charcoal, filtered and acidified with 3.6N anhydrous hydrogen chloride in diethyl ether to afford the hydrochloride. M.p. 213–216° C.

| $^1$H-NMR (200 MHz, CDCl$_3$, δ) | | | |
|---|---|---|---|
| 10.05 | bs | 2H | NH$_2^-$ |
| 7.13 | dd | 1H | H4 of phenyl ring |
| 6.96 | dd | 1H | H6 of phenyl ring |
| 6.79 | d | 1H | H3 of phenyl ring |
| 4.34 | q | 2H | CF$_3$CH$_2$O |
| 3.41 | bs | 8H | piperazine CH$_2$s | d) 8-<3-{4-[5-Chloro-2-(2,2,2-trifluoroethoxy)phenyl]-1-piperazinyl}-1-propylcarbamoyl>3-methyl-4-oxo-2-phenyl-4H-1-benzopyran The title compound was prepared following the procedure described in Ex. 15, substituting Compound 22C for 1-[2-(2,2,2-trifluoroethoxy)phenyl]piperazine. Flash chromatography was carried out using ethyl acetate/methanol, gradient 100:0 to 100:2, and crystallisation was from ethanol. Yield 48.8%, as a white solid. M.p. 179–182° C.

| $^1$H-NMR (200 MHz, CDCl$_3$, δ) | | | |
|---|---|---|---|
| 8.39 | d | 2H | H5 and H7 |
| 7.65–7.80 | m | 2H | H6 and H2 of 2-phenyl ring |
| 7.55–7.65 | m | 4H | H3, H4 and H5 of 2-phenyl ring CONH |
| 7.49 | dd | 1H | H6 |
| 6.92 | dd | 1H | Chlorophenyl H4 |
| 6.72–6.85 | m | 2H | Chlorophenyl H3 and H6 |
| 4.33 | q | 2H | CF$_3$CH$_2$O |
| 3.47–3.55 | m | 2H | CONHCH$_2$CH$_2$CH$_2$ |
| 2.80–3.05 | m | 4H | 2 piperazine CH$_2$s |
| 2.30–2.55 | m | 6H | 2 piperazine CH$_2$s, CONHCH$_2$CH$_2$CH$_2$ |
| 2.21 | s | 3H | CH$_3$ |
| 1.59–1.75 | m | 2H | CONHCH$_2$CH$_2$CH$_2$ |

EXAMPLE 23

8-{3-[4-(5-Carbamoyl-2-methoxyphenyl)-1-piperazinyl]propylcarbamoyl}-3-methyl-4-oxo-2-phenyl-4H-1-benzopyran a) 1-(5-Carbamoyl-2-methoxyphenyl)piperazine. 0.35 $H_2O$ (Compound 23A)

A mixture of 0.482 g of Compound 18C and 8 mL of 95–98% sulphuric acid was stirred at room temperature for 1 hour. After overnight resting, the solution was poured into cold water, alkalinised with 35% sodium hydroxide and extracted with 3×30 mL of ethyl acetate. The organic layer was washed with 20 mL of brine and dried over sodium sulphate, and the solvent was evaporated off in vacuo. The crude was purified by flash chromatography (chloroform/2N methanolic ammonia, gradient from 100:10 to 100:20) to afford 0.23 g (44%) of Compound 23A as an ivory solid. M.p. 167–176° C.

| $^1$H-NMR (200 MHz, CDCl$_3$, δ) | | | |
|---|---|---|---|
| 7.42–7.50 | m | 2H | H6 and H4 |
| 6.85 | d | 1H | H3 |
| 5.88 | bs | 2H | CONH$_2$ |
| 3.91 | s | 3H | CH$_3$O |
| 3.00–3.10 | m | 8H | piperazine CH$_2$s |
| 2.03 | bs | 1.7H | NH, 0.35 H$_2$O | b) 8-{3-[4-(5-Carbamoyl-2-methoxyphenyl)-1-piperazinyl] propylcarbamoyl}-3-methyl-4-oxo-2-phenyl-4H-1-benzopyran The title compound was prepared following the procedure described in Ex. 15, but substituting Compound 23A for 1-[2-(2,2,2-trifluoroethoxy)phenyl]piperazine. The residue was purified by flash chromatography (chloroform/2N methanolic ammonia, gradient from 100:5 to 100:8) to afford the title compound (40%) as a solid. M.p. 78–86° C.

| $^1$H-NMR (200 MHz, CDCl$_3$, δ) | | | |
|---|---|---|---|
| 8.38–8.42 | m | 2H | H5 and H7 |
| 7.90–8.01 | m | 1H | CONH |
| 7.66–7.78 | m | 2H | H2 and H6 of 2-phenyl ring |
| 7.50–7.64 | m | 3H | H3, H4 and H5 of 2-phenyl ring |
| 7.47 | t | 1H | H6 |
| 7.43 | dd | 1H | methoxyphenyl H4 |
| 7.25 | d | 1H | methoxyphenyl H6 |
| 6.83 | d | 1H | methoxyphenyl H3 |
| 5.40–6.40 | br | 2H | CONH$_2$ |
| 3.88 | s | 3H | CH$_3$O |
| 3.48–3.65 | m | 2H | CONHC$\underline{H}_2$CH$_2$CH$_2$ |
| 2.25–2.45 | m | 4H | 2 piperazine CH$_2$s |
| 2.31–2.52 | m | 6H | 2 piperazine CH$_2$s, CONHCH$_2$CH$_2$C$\underline{H}_2$ |
| 2.21 | s | 3H | CH$_3$ |
| 1.58–1.80 | m | 2H | CONHCH$_2$C$\underline{H}_2$CH$_2$ |

EXAMPLE 24

8-{3-[4-(5-Chloro-2-trifluoromethanesulphonyloxyphenyl)-1-piperazinyl]-propylcarbamoyl}-3-methyl-4-oxo-2-phenyl-4H-1-benzopyran hydrochloride a) 8-{3-[4-(5-Chloro-2-hydroxyphenyl)-1-piperazinyl] propylcarbamoyl}-3-methyl-4-oxo-2-phenyl-4H-1-benzopyran (Compound 24A)

The title compound was prepared following the procedure described in Ex. 15, but using Compound 12A instead of 1-[2-(2,2,2-trifluoroethoxy)phenyl]piperazine. The residue was purified by flash chromatography (chloroform/3N methanolic ammonia 100:1). The solvent was removed in vacuo and the residue was crystallised from acetonitrile to afford Compound 24A (38.8%). M.p. 13.9–141° C. (150° C.).

| $^1$H-NMR (200 MHz, DMSO-d$_6$, δ) | | | |
|---|---|---|---|
| 9.34 | s | 1H | OH |
| 8.42–8.62 | m | 1H | CONH |
| 8.18 | dd | 1H | H5 (7) |
| 7.90 | dd | 1H | H7 (5) |
| 7.70–7.85 | m | 2H | H2 and H6 of 2-phenyl ring |
| 7.52–7.60 | m | 4H | H6; H3, H4 and H5 of 2-phenyl ring |
| 6.55–6.90 | m | 3H | H3, H4 and H6 of hydroxyphenyl ring |
| 3.20–3.40 | m | 2H | CONHC$\underline{H}_2$CH$_2$CH$_2$ |
| 2.80–3.05 | m | 4H | 2 piperazine CH$_2$s |
| 2.20–2.48 | m | 6H | 2 piperazine CH$_2$s, CONHCH$_2$CH$_2$C$\underline{H}_2$ |
| 2.08 | s | 3H | CH$_3$ |
| 1.50–1.75 | m | 2H | CONHCH$_2$C$\underline{H}_2$CH$_2$ | b) 8-{3-[4-(5-Chloro-2-trifluoromethanesulphonyloxyphenyl)-1-piperazinyl]-propylcarbamoyl}-3-methyl-4-oxo-2-phenyl-4H-1-benzopyran hydrochloride The title compound was synthesised following the method described in Ex. 14, but substituting Compound 24A for 8-{3-[4-(2-hydroxyphenyl)-1-piperazinyl]-propylcarbamoyl}-3-methyl-4-oxo-2-phenyl-4H-1-benzopyran. The flash chromatography was carried out in chloroform/methanol 100:2. The solvent was removed in vacuo to give a residue that was dissolved in diethyl ether. The solution was treated with charcoal and filtered to afford a clear solution which was made acidic with 3N anhydrous hydrogen chloride in diethyl ether. The resultant suspension was kept overnight at room temperature, then the solid was collected by filtration and crystallised from acetonitrile to afford the title Compound (52.3%). M.p. 203–210° C.

| $^1$H-NMR (200 MHz, DMSO-d$_6$, δ) | | | |
|---|---|---|---|
| 10.88–11.20 | br | 1H | NH$^+$ |
| 8.63–8.80 | m | 1H | CONH |
| 8.20 | dd | 1H | H5 (7) |
| 7.96 | dd | 1H | H7 (5) |
| 7.70–7.89 | m | 2H | H2 and H6 of 2-phenyl ring |
| 7.15–7.70 | m | 7H | H6; 2-phenyl H3, H4 and H5, chlorophenyl H3, H4 and H6 |
| 3.05–3.60 | m | 10H | piperazine CH$_2$s, CONHC$\underline{H}_2$CH$_2$CH$_2$ |
| 2.75–3.05 | m | 2H | CONHCH$_2$CH$_2$C$\underline{H}_2$ |
| 2.09 | s | 3H | CH$_3$ |
| 1.80–2.05 | m | 2H | CONHCH$_2$C$\underline{H}_2$CH$_2$ |

EXAMPLE 25

2-Phenyl-8-<2-{4-[2-(2,2,2-trifluoroethoxy)phenyl]-1-piperazinyl}-ethylcarbamoyl>-3-methyl-4-oxo-4H-1-benzopyran A mixture of 0.3 g of 8-(2-chloroethylcarbamoyl)-2-phenyl-3-methyl-4-oxo-4H-1-benzopyran (prepared as described in U.S. Pat. No. 5,403,082, Leonardi et al.), 0.35 g of 1-[2-(2,2,2-trifluoroethoxy)phenyl]piperazine (prepared as described in European Patent EP 748800, Bantle et al.) and 0.3 mL of triethylamine was heated to 160–180° C. The reaction mixture was cooled to room temperature and purified by flash chromatography eluting with toluene/acetone 85:15 to afford 0.42 g (85%) of the title compound. M.p. 188.5–189.5° C.

| $^1$H-NMR (200 MHz, CDCl$_3$, δ) | | |
|---|---|---|
| 8.43 | d | 2H H5 and H7 |
| 7.66–7.78 | m | 2H H2 and H6 of 2-phenyl ring |
| 7.50–7.61 | m | 4H H3, H4 and H5 of 2-phenyl ring, H6 |
| 7.41 | bs | 1H CONH |
| 6.81–7.11 | m | 4H H3, H4, H5 and H6 of trifluoroethoxyphenyl ring |
| 4.37 | q | 2H OCH$_2$CF$_3$ |
| 3.61 | q | 2H CONHC$\underline{H}_2$CH$_2$N |
| 2.75–2.90 | m | 4H 2 piperazine CH$_2$s |
| 2.50 | t | 2H CONHCH$_2$C$\underline{H}_2$N |
| 2.27–2.39 | m | 4H 2 piperazine CH$_2$s |
| 2.19 | s | 3H CH$_3$ |

Pharmacological Data

EXAMPLE 26

Determination of Affinity for Cloned $\alpha_1$-adrenoceptor Sutaypes ($\alpha_{1a}$, $\alpha_{1b}$, $\alpha_{1d}$) and 5-HT$_{1A}$-serotoninergic Receptors by Radioligand Binding Assay Determination of affinity for cloned subtypes of $\alpha_1$-adrenoceptor subtypes was performed in membranes from cells transfected by electroporation with DNA expressing the genes encoding each $\alpha_1$-adrenoceptor subtype.

Cloning and stable expression of the $\alpha_1$-adrenoceptor gene were performed as previously described (Testa R. et al., *Pharmacol. Comm.* 6: 79–86, 1995 and references). The cell to membranes were incubated in 50 mM Tris, pH 7.4, with 0.2 nM [$^3$H]prazosin, in a final volume of 1.02 mL for 30 minutes at 25° C., in the absence or presence of competing drugs (1 pM–10 μM). Non-specific binding was determined in the presence of 10 μM phentolamine.

Incubation was stopped by addition of ice-cold Tris buffer and rapid filtration through 0.2% polyethyleneimine-pretreated Schleicher & Schuell GF52 filters.

Genomic clone G-21 coding for the human 5-HT$_{1A}$-serotoninergic receptor was stably transfected in a human cell line (HeLa) (Fargin A. et al., *J. Biol. Chem.* 284: 14848–14852, 1989). HeLa cells were grown as monolayers in Dulbecco's Modified Eagle medium (DMEM) supplemented with 10% foetal calf serum and gentamicin (100 μg/mL), 5% CO$_2$, at 37° C. The cells were detached from the growth flask at 95% confluence by a cell scraper and were lysed in ice-cold Tris-5-mM and EDTA-5-mM buffer (pH 7.4). The homogenates were centrifuged at 40000×g×20 minutes and the membranes were resuspended in a small volume of ice-cold buffer containing Tris 5 mM and EDTA 5 mM (pH 7.4), and immediately frozen and stored at −70° C. until use.

On the day of the experiment, the cell membranes were resuspended in a buffer containing 50 mM Tris (pH 7.4), 2.5 mM MgCl$_2$, 10 μM pargyline (Fargin et al, *Nature* 335; 358–360, 1988). The membranes were incubated in a final volume of 1 mL for 30 minutes at 30° C. with 1.2 nM [$^3$H]8-OH-DPAT, in the absence or presence of test molecules. Non-specific binding was determined in the presence of 10 μM 5-HT. The incubation was stopped by addition of ice-cold Tris buffer and rapid filtration through 0.2% polyethyleneimine-pretreated Schleicher & Schuell filters.

Inhibition of specific binding of the radioligands by the test drugs was analysed to estimate the IC$_{50}$ value by using the non-linear curve-fitting program Allfit (De Lean A. et al., *Am. J. Physiol.* 235: E97–E102, 1978).

The IC$_{50}$ value was converted to an affinity constant (Ki) by the equation of Cheng et al. (*Biochem. Pharmacol.* 22: 3099–3108, 1973). Data were expressed as mean Ki.

Results

The compounds of the invention exhibited the desired potency and selectivity at $\alpha_1$-adrenoceptors, as shown in Table 1.

TABLE 1

Affinity of the different compounds tested for recombinant $\alpha_1$-adrenoceptor subtypes and 5-HT$_{1A}$ receptor.

| | Cloned receptors (Ki, nM) | | | |
|---|---|---|---|---|
| Example | $\alpha_{1a}$ | $\alpha_{1b}$ | $\alpha_{1d}$ | 5-HT$_{1A}$ |
| 1 | 2.40 | 2.62 | 57.44 | 17.20 |
| 2 | 0.32 | 2.34 | 2.68 | 12.30 |
| 3 | 0.20 | 0.32 | 0.45 | 81.87 |
| 4 | 0.21 | 0.08 | 2.75 | 15.23 |
| 5 | 0.57 | 2.39 | 2.05 | 23.10 |
| 6 | 0.23 | 3.56 | 3.83 | 68.38 |
| 7 | 1.01 | | 6.43 | 12.79 |
| 8 | 0.144 | 9.91 | 3.02 | 39.54 |
| 9 | 28.64 | 94.75 | 467.23 | >1000 |
| 10 | 0.173 | 14.32 | 6.53 | 5.54 |
| 11 | 0.38 | 0.78 | 2.72 | 24.38 |
| 12 | 1.15 | 2.02 | 9.96 | 4.16 |
| 13 | 1.61 | 1.00 | 11.04 | 31.39 |
| 15 | 0.07 | 6.00 | 3.38 | 0.71 |
| 17 | 1.60 | 9.42 | 13.11 | |
| 18 | 4.18 | 100.40 | 45.38 | 677.06 |
| 19 | 0.136 | 2.61 | 4.79 | 22.45 |
| 20 | 0.07 | 3.54 | 0.32 | 4.46 |
| 21 | 2.54 | 31.63 | 34.70 | 257.20 |
| 22 | 0.25 | 1.90 | 3.07 | |
| 24 | 4.21 | 7.80 | 33.74 | 139.89 |
| Compound A | 0.65 | 3.87 | 1.51 | 4.53 |
| Prazosin | 0.54 | 0.42 | 0.23 | 10000 |
| Terazosin | 6.90 | 2.20 | 2.40 | |

EXAMPLE 27

In vitro Determination of Functional Antagonism for $\alpha_{1L}$-adrenoceptors

The functional $\alpha_1$-antagonistic activity of the test compounds against noradrenaline (NA)-induced contractions of rabbit aorta pretreated with chloroethylclonidine ($\alpha_{1L}$ receptor) was evaluated according to the method of Testa et al. (*J. Pharmacol. Exp. Ther.* 281:, 1284–1293, 1997).

Adult male New Zealand rabbits were sacrificed by cervical dislocation. The aorta was removed, placed in Krebs-Henseleit buffer and dissected free of adhering tissue. Rings were prepared from each artery (8 rings per aorta, about 4–5 mm wide) and suspended in 20 mL organ bath containing Krebs bicarbonate buffer of the following composition: 112.0 mM NaCl, 5.0 mM KCl, 2.5 mM CaCl$_2$, 1.0 mM KH$_2$PO$_4$, 1.2 mM MgSO$_4$, 12.0 mM NaHCO$_3$ and 11.1 mM glucose, equilibrated at 37° C. with 95% O$_2$: 5% CO$_2$. Desmethylimipramine (0.1 μm) and corticosterone (1 μM) to block neuronal and extraneuronal uptake of NA, (±)-propranol (1 μM) to block β adrenoceptors and yohimbine (0.1 μM) to block $\alpha_2$ adrenoceptors, were added to the buffer.

The tissues were subjected to a passive load of 2 g and the developed tension was measured using isometric transducers (Basile 7003). The preparations were allowed to equilibrate for 60 minutes and then primed every thirty minutes with 10 μM NA for three times. The aortic rings were then incubated with the alkylating agent chloroethylclonidine (5×10$^{-5}$ M) for 30 minutes and then washed extensively three times (in 0.5 hours) before constructing the NA-concentration/response curve. After washout of NA and re-equilibration of the tissue (45 minutes), the drug to be tested was added and, after 30 minutes, a second NA-cumulative-concentration/response curve constructed.

Each antagonist concentration was tested using 2–3 aortic rings from different rabbits.

Dose ratios (i.e., the ratio between the concentrations of NA required to produce half-maximal response in the presence and in the absence of the test antagonist) were calculated for each concentration of the compounds. The logarithm of these dose ratio-1 was plotted against the logarithm of the compound concentrations (Schild plot) to evaluate the affinity constant Kb.

When only one or two concentrations of the test compounds were utilised, the apparent Kb value was calculated using the formula: Kb=[B]/(DOSE RATIO-1), where B is the antagonist concentration.

The compounds tested showed good affinity for the $\alpha_{1L}$ adrenoceptor subtype. The data are expressed as pKb in Table 2.

TABLE 2

Functional affinity of the tested compounds for the $\alpha_{1l}$ adrenoceptor subtype.

| Example | pKb |
| --- | --- |
| 1 | 8.27 |
| 3 | 8.43 |
| 4 | 8.47 |
| 6 | 8.55 |
| 8 | 9 |
| 11 | 8.45 |
| 15 | 8.19 |
| 17 | 8.03 |
| 19 | 8.72 |
| Compound A | 8.91 |
| Prazosin | 7.68 |
| Terazosin | 7.25 |

EXAMPLE 28

Effects on Urethral Contractions Induced by Noradrenaline Injection and on Blood Pressure in Dogs after I.V. Administration The experiments were performed according to the method of Imagawa J. et al., *J. Pharmacol. Methods* 22: 103–111, 1989, with substantial modifications, as follows: adult male beagle dogs, weighing 8–10 kg, were anaesthetised with pentobarbital sodium (30 mg/kg i.v. and 2 mg/kg/h i.v.), intubated and spontaneously ventilated with room air. In order to monitor systemic blood pressure (BP), a polyethylene (PE) catheter was introduced into the aortic arch through the left femoral artery. A collateral of the left femoral vein was cannulated for infusion of anaesthetic, and the right femoral vein was cannulated for administration of compounds. For intra-arterial (i.a.) injection of noradrenaline (NA), a PE catheter was introduced into the lower portion of the abdominal aorta via the right external iliac artery. Through such procedure, NA was selectively distributed to the lower urinary tract. A paramedian vertical suprapubic incision extending from the base of the pelvis to the mid-abdominal region was made and the bladder and prostate were exposed. The bladder was manually emptied with a syringe. Prostatic urethral pressure was monitored with a Mikro-tip catheter (5F) introduced into the bladder via the external urethral meatus, and withdrawn until the pressure transducer was positioned in the prostatic region of the urethra. A ligature was secured between the neck of the bladder and urethra to isolate the response of the latter and to avoid any interaction with the bladder. Another ligature was put around the Mikro-tip catheter at the external meatus, to secure the catheter itself. After a stabilising period following the surgical procedure (30 minutes), in which arterial and prostatic urethral pressure were continuously monitored as basal values, i.a. administration of NA was made at intervals of 20 minutes. The doses of NA chosen were such to produce an increase of at least 100% in urethral pressure. The test compounds were administered i.v. in a cumulative manner with intervals of 15–20 minutes between administrations. I.a. injections of NA were repeated 5 minutes after every dosing of test compound with intervals of about 10 minutes between stimulations. In order to compare the effects of the administered compound, dose/response curves (log dose transformation) were constructed by computing, at the peak effect, the percent decrease in diastolic blood pressure and the percent inhibition of the increase in urethral pressure induced by NA. Linear regression equations were then used in order to evaluate the theoretical effectiveness as $ED_{25}$ (the effective dose inducing a 25% decrease in diastolic blood pressure) and $ID_{50}$ (the dose inhibiting by 50% the increase in urethral pressure).

The effects obtained after iv. administration of the compounds of the examples are shown in Table 3. The results concerning the effects obtained after injection of prazosin, terazosin and Rec 15/2739 are also shown in the Table.

TABLE 3

Data represent the active doses (expressed in μg/kg) inhibiting by 50% the urethral contractions (UC) induced by noradrenaline (NA), the active doses (expressed in μg/kg) in lowering diastolic blood pressure (DBP) by 25% and the ratio (DBP/UC) between the active doses

| Example | UC $ID_{50}$ | DBP $ED_{25}$ | DBP/ UC |
| --- | --- | --- | --- |
| 1 | 11.8 | 2769 | 234.7 |
| 4 | 2.3 | 163.3 | 71.0 |
| 15 | 4.9 | 3001 | 612 |
| 18 | 34.1 | 1297.6 | 38.05 |
| 22 | 19.5 | 1266 | 64.92 |
| Prazosin* | 3.6 | 6.6 | 1.83 |
| Terazosin* | 20.6 | 61.4 | 2.98 |
| Compound A* | 2.4 | 243 | 101.2 |

*Data from Leonardi et al. J Pharmacol. Exp. Ther. 281: 1272–1283, 1997

EXAMPLE 29

Evaluation of the Duration of Action on Inhibition of Urethral Contractions Induced by i.v. Noradrenaline Injection in Dogs The dog model described in Ex. 28 was used. To evaluate the duration of inhibition of the increase in urethral pressure, NA stimulation was repeated at 5, 30, 60, 90, 120, 180 and 240 minutes. The experimental data of the compound of Ex. 15 (30 μg/kg) compared to Compound A (10 μg/kg) are shown in FIG. 1.

The pharmacological results obtained in Ex. 26–29 show that the compounds of the invention are $\alpha_1$-adrenoceptor antagonists with good selectivity for the $\alpha_1$ adrenoceptor in particular versus the $5HT_{1A}$ receptor, and good affinity also for the $\alpha_{1L}$ subtype, as far as in vitro data are concerned. The in vivo pharmacological results confirm the extremely high uroselectivity of the compounds of the invention as well as the long duration of the effect, and justify their possible use in the treatment of obstructive and non-obstructive diseases of the lower urinary tract, including BPH obstructive symptoms, LUTS (in males and females) and NLUTD, with limited effect on the cardiovascular system.

Effective Amounts

The term "effective amount" and "therapeutically effective amount" is that amount of the compound or composition determined by the skilled artisan to effectively prevent or treat the targeted disease condition. The effective amount of a compound or composition will be determined empirically by administering a range of dosages to the patient and observing that dosage which is most effective for the treatment of the condition and best tolerated by the patient. The method of making such a determination will be readily understood by the skilled artisan and will necessarily take into account such factors as, inter alia, the route of administration, formulation, and the condition, age, sex, height, and weight of the patient.

The following represent guidelines to effective oral, parenteral or intravenous dose ranges for human hosts, expressed in mg/kg of body weight per day, for the use in disorders of the lower urinary tract:

| general | 0.001–20 |
| preferred | 0.05–3 |
| most preferred | 0.5–2 |

The most-preferred values refer to oral dosing. Intravenous dosages should be 10 to 100 fold lower. Selective-use dosages, i.e., dosages that are active in the lower urinary tract without a substantial effect on blood pressure, depend on the particular compound employed. Generally, in the case of a compound selective in inhibiting urethral contraction, up to four times the amount of the $ED_{50}$ used in inhibiting urethral contraction can be administered without substantial effect on blood pressure. Further refinements and optimization of dosages are possible using no more than routine experiments. The active compounds of the invention may be orally administered, for example, with an inert diluent or with an edible carrier, or they may be enclosed in gelatine capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but the amount of active ingredient may be varied depending upon the particular form and may conveniently be between 5% and about 70% of the weight of the unit. The amount of active compound in such compositions is such that a suitable dosage will be obtained although the desired dosage can be obtained by administering a plurality of dosage forms. The preferred compositions and preparations according to the invention are prepared so that an oral dosage unit form contains between 1.0 and 300 milligrams of active compound. The tablets, pills, capsules, troches and the like may also contain, for example, the following ingredients: a binder such as microcrystalline cellulose, gum tragacanth or gelatine; an excipient such as starch or lactose; a disintegrating agent such as alginic acid, sodium starch glycolate, cornstarch and the like; a lubricant such as magnesium stearate or hydrogenated castor oil, a glidant such as colloidal silicon dioxide; a sweetening agent such as sucrose or saccharin; and a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example coatings. Thus, tablets or pills may be coated with sugar, shellac, or other enteric-coating agents. A syrup may contain, in addition to the active compounds, sucrose as a sweetening agent and certain preservatives, dyes, colouring and flavors. The materials used in preparing these various compositions should be pharmaceutically pure and non-toxic in the amounts used. For the purpose of parenteral therapeutic administration, the active compounds of the invention may be incorporated into a solution or suspension. These preparations should contain at least 0.1% of active compound, but this may vary between 0.5 and about 30% of the weight thereof. The amount of active compound in such compositions is such that a suitable dosage will be obtained. The preferred compositions and preparations according to the present inventions are prepared so that a parenteral dosage unit contains between 0.2 and 100 milligrams of active compound. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulphite; chelating agents such as ethylenediaminetetraacetic acid; buffers such as acetates; citrates or phosphates and agents for the adjustment of tonicity such as sodium chloride or dextrose. The parenteral multiple dose vials may be of glass or plastics material. The frequency of administration of the present compounds and compositions may be adjusted based on need and physician's advice but will typically be once or twice a day the duration of treatment will be while symptoms persist, even indefinitely.

Additional compositions suitable for administration by various routes and containing compounds according to the present invention are also within the scope of the invention. Dosage forms, additional ingredients and routes of administration contemplated herein include those disclosed in U.S. Pat. No. 4,089,969 (Muchowski et al.), and U.S. Pat. No. 5,091,182 (Ong). Both of these patents are incorporated by reference in their entirety.

All U.S. patents and other references listed herein are hereby incorporated by reference. In case of conflict in definitions, the present disclosure controls.

What is claimed is:

1. A compound of the formula

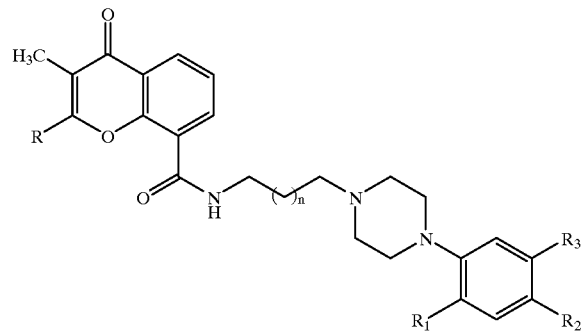

wherein

R is selected from the group consisting of a phenyl, alkoxycarbonyl, alkylcarbonyl, carbamoyl, alkylcarbamoyl, dialkylcarbamoyl, cyano and alkoxycarbonylamino group, $R_1$ is selected from the group consisting of an alkyl, alkoxy, polyfluoroalkoxy, hydroxy and trifluoromethanesulphonyloxy group, each of $R_2$ and $R_3$ is independently selected from the group consisting of hydrogen, halogen, polyfluoroalkyl, polyfluoroalkoxy, cyano, or carbamoyl group, and n is 0, 1 or 2, with the proviso that if R represents a phenyl group and both $R_2$ and $R_3$ represent hydrogen and/or halogen atoms, then $R_1$ represents a polyfluoroalkoxy or trifluoromethanesulphonyloxy group, or an N-oxide or pharmaceutically acceptable salt of such a compound.

2. A compound according to claim 1 wherein R is selected from the group consisting of alkoxycarbonyl, alkylcarbonyl, carbamoyl, alkylcarbamoyl, dialkylcarbamoyl, cyano, and alkoxycarbonylamino and $R_2$ and $R_3$ are independently selected from hydrogen, halogen and polyfluoroalkoxy group.

3. A compound according to claim 1 wherein $R_1$ is selected from the group consisting of methyl, methoxy, trifluoromethoxy, 2,2,2-trifluoroethoxy, hydroxy and trifluoromethanesulphonyloxy group.

4. A compound according to claim 1 wherein $R_2$ is selected from the group consisting of hydrogen and fluorine.

5. A compound according to claim 1 wherein $R_3$ is selected from the group consisting of hydrogen, fluorine, chlorine, trifluoromethyl, 2,2,2-trifluoroethoxy, cyano and carbamoyl.

6. A compound according to claim 5 wherein $R_3$ is selected from the group consisting of hydrogen, fluorine, chlorine and 2,2,2-trifluroethoxy.

7. A compound according to claim 1 wherein n=1.

8. A compound selected from the group consisting of
2-carbamoyl-8-{3-[4-(5-chloro-2-methoxyphenyl)-1-piperazinyl]-propylcarbamoyl}-3-methyl-4-oxo-4H-1-benzopyran,
2-acetyl-8-{3-[4-(5-chloro-2-methoxyphenyl)-1-piperazinyl]-propylcarbamoyl}-3-methyl-4-oxo-4H-1-benzopyran,
8-{3-[4-(5-chloro-2-methoxyphenyl)-1-piperazinyl] propylcarbamoyl}-2-(1,1-dimethylethoxycarbonylamino)-3-methyl-4-oxo-4H-1-benzopyran,
8-{3-[4-(5-chloro-2-methoxyphenyl)-1-piperazinyl]-propylcarbamoyl}-2-ethoxycarbonyl-3-methyl-4-oxo-4H-1-benzopyran,
8-{3-[4-(5-chloro-2-methoxyphenyl)-1-piperazinyl] propylcarbamoyl}-3-methyl-2-methylcarbamoyl-4-oxo-4H-1-benzopyran,
8-{3-[4-(5-chloro-2-methoxyphenyl)-1-piperazinyl] propylcarbamoyl}-3-methyl-2-dimethylcarbamoyl-4-oxo-4H-1-benzopyran,
2-carbamoyl-8-{3-[4-[4-fluoro-2-(2,2,2-trifluoroethoxy) phenyl]-1-piperazinyl]propylcarbamoyl}-3-methyl-4-oxo-4H-1-benzopyran,
2-carbamoyl-8-{3-[4-[5-fluoro-2-(2,2,2-trifluoroethoxy) phenyl]-1-piperazinyl]propylcarbamoyl}-3-methyl-4-oxo-4H-1-benzopyran,
2-carbamoyl-8-{3-[4-[2-methoxy-5-(2,2,2-trifluoroethoxy)phenyl]-1 -piperazinyl] propylcarbamoyl}-3-methyl-4-oxo-4H-1-benzopyran,
2-carbamoyl-3-methyl-4-oxo-8-{3-[4-[2-(2,2,2-trifluoroethoxy)phenyl]-1-piperazinyl] propylcarbamoyl}-4H-1-benzopyran,
8-{3-[4-(5-chloro-2-methoxyphenyl)-1-piperazinyl] propylcarbamoyl}-2-cyano-3-methyl-4-oxo-4H-1-benzopyran,
2-carbamoyl-8-{3-[4-(5-chloro-2-hydroxyphenyl)-1-piperazinyl]-propylcarbamoyl}-3-methyl-4-oxo-4H-1-benzopyran,
2-carbamoyl-8-{3-[4-(5-chloro-2-trifluoromethanesulphonyloxyphenyl)-1-piperazinyl] propylcarbamoyl}-3-methyl-4-oxo-4H-1-benzopyran,
3-methyl-4-oxo-2-phenyl-8-{3-[4-(2-trifluoromethanesulphonyloxyphenyl)-1-piperazinyl]-propylcarbamoyl}-4H-1-benzopyran,
3-methyl-4-oxo-2-phenyl-8-{3-[4-[2-(2,2,2-trifluoroethoxy)phenyl]-1-piperazinyl] propylcarbamoyl}-4H-1-benzopyran,
3-methyl-4-oxo-2-phenyl-8-{3-[4-(2-trifluoromethoxyphenyl)-1-piperazinyl] propylcarbamoyl}-4H-1-benzopyran,
8-{3-[4-(2-methoxy-5-trifluoromethylphenyl)-1-piperazinyl]-propylcarbamoyl}-3-methyl-4-oxo-2-phenyl-4H-1-benzopyran,
8-{3-[4-(5-cyano-2-methoxyphenyl)-1-piperazinyl] propylcarbamoyl}-3-methyl-4-oxo-2-phenyl-4H-1-benzopyran,
8-{3-[4-[4-fluoro-2-(2,2,2-trifluoroethoxy)phenyl]-1-piperazinyl]-propylcarbamoyl}-3-methyl-4-oxo-2-phenyl-4H-1-benzopyran,
8-{3-[4-[5-fluoro-2-(2,2,2-trifluoroethoxy)phenyl]-1-piperazinyl]-propylcarbamoyl}-3-methyl-4-oxo-2-phenyl-4H-1-benzopyran,
8-{3-[4-[2-methoxy-5-(2,2,2-trifluoroethoxy)phenyl]-1-piperazinyl]-propylcarbamoyl}-3-methyl-4-oxo-2-phenyl-4H-1-benzopyran,
8-{3-[4-[5-chloro-2-(2,2,2-trifluoroethoxy)phenyl]-1-piperazinyl]-propylcarbamoyl}-3-methyl-4-oxo-2-phenyl-4H-1-benzopyran,
8-{3-[4-(5-carbamoyl-2-methoxyphenyl)-1-piperazinyl] propylcarbamoyl}-3-methyl-4-oxo-2-phenyl-4H-1-benzopyran,
8-{3-[4-(5-chloro-2-trifluoromethanesulphonyloxyphenyl)-1-piperazinyl]-propylcarbamoyl}-3-methyl-4-oxo-2-phenyl-4H-1-benzopyran, and
3-methyl-4-oxo-phenyl-8-{2-[4-[2-(2,2,2-trifluoroethoxy)phenyl]-1-piperazinyl]-ethylcarbamoyl}-4H-1-benzopyran;
or an N-oxide or pharmaceutically acceptable salt of such a compound.

9. A composition comprising a compound according to claim 1 and a pharmaceutically acceptable diluent or carrier.

10. A composition comprising a compound according to claim 8 and a pharmaceutically acceptable diluent or carrier.

11. A method for treating contractions of the urethra and lower urinary tract, the method comprising administering a compound according to claim 1 to a mammal in need of such treatment in an amount effective for treating said contractions.

12. A method for treating contractions of the urethra and lower urinary tract, the method comprising administering a compound according to claim 8 to a mammal in need of such treatment in an amount effective for treating said contractions.

13. A method according to claim 11 wherein the administration of said compound causes limited effects on the blood pressure of said mammal.

14. A method according to claim 12 wherein the administration of said compound causes limited effects on the blood pressure of said mammal.

15. The method of claim 11 wherein said mammal is a human.

16. The method of claim 12 wherein said mammal is a human.

17. The method of claim 13 wherein said mammal is a human.

18. The method of claim 14 wherein said mammal is a human.

19. A method for the treatment of a patient suffering from benign prostatic hyperplasia, the method comprising administering an effective amount of a compound according to claim 1 to a patient in need of such treatment.

20. A method for the treatment of a patient suffering from benign prostatic hyperplasia, the method comprising administering an effective amount of a compound according to claim 8 to a patient in need of such treatment.

21. A method for the treatment of a patient suffering from excessive intraocular pressure, the method comprising administering an effective amount of a compound according to claim 1 to a patient in need of such treatment.

22. A method for the treatment of a patient suffering from excessive intraocular pressure, the method comprising administering an effective amount of a compound according to claim 8 to a patient in need of such treatment.

23. A method for the treatment of a patient suffering from cardiac arrhythmia, the method comprising administering an effective amount of a compound according to claim 1 to a patient in need of such treatment.

24. A method for the treatment of a patient suffering from cardiac arrhythmia, the method comprising administering an effective amount of a compound according to claim 8 to a patient in need of such treatment.

25. A method for the treatment of a patient suffering from erectile dysfunction, the method comprising administering an effective amount of a compound according to claim 1 to a patient in need of such treatment.

26. A method for the treatment of a patient suffering from erectile dysfunction, the method comprising administering an effective amount of a compound according to claim 8 to a patient in need of such treatment.

27. A method for the treatment of a patient suffering from sexual dysfunction, the method comprising administering an effective amount of a compound according to claim 1 to a patient in need of such treatment.

28. A method for the treatment of a patient suffering from sexual dysfunction, the method comprising administering an effective amount of a compound according to claim 8 to a patient in need of such treatment.

29. A method for inhibiting cholesterol biosynthesis in a patient, the method comprising administering an effective amount of a compound according to claim 1 to a patient in need thereof.

30. A method for inhibiting cholesterol biosynthesis in a patient, the method comprising administering an effective amount of a compound according to claim 8 to a patient in need thereof.

31. A method for reducing sympathetically mediated pain in a patient, the method comprising administering an effective amount of a compound according claim 1 to a patient in need thereof.

32. A method for reducing sympathetically mediated pain in a patient, the method comprising administering an effective amount of a compound according to claim 8 to a patient in need thereof.

33. A method for the treatment of lower urinary tract symptoms in a patient, the method comprising administering an effective amount of a compound according to claim 1 to a patient in need of such treatment.

34. A method for the treatment of lower urinary tract symptoms in a patient, the method comprising administering an effective amount of a compound according to claim 8 to a patient in need of such treatment.

35. The method according to claim 33 wherein said patient is a female.

36. The method according to claim 34 wherein said patient is a male.

37. A method for the treatment of neurogenic lower urinary tract dysfunction in a patient, the method comprising administering an effective amount of a compound according to claim 1 to a patient in need of such treatment.

38. A method for the treatment of neurogenic lower urinary tract dysfunction in a patient, the method comprising administering an effective amount of a compound according to claim 8 to a patient in need of such treatment.

* * * * *